US008389599B2

(12) United States Patent  
Yang et al.

(10) Patent No.: US 8,389,599 B2  
(45) Date of Patent: Mar. 5, 2013

(54) DENTAL COMPOSITION COMPRISING BIPHENYL DI(METH)ACRYLATE MONOMER COMPRISING URETHANE MOIETIES

(75) Inventors: Jie Yang, Woodbury, MN (US); Naimul Karim, Maplewood, MN (US); David B. Olson, Marine on St. Croix, MN (US); Todd D. Jones, St. Paul, MN (US); Dwight W. Jacobs, Hudson, WI (US)

(73) Assignee: 3M Innovative Properties Company, St. Paul, MN (US)

( * ) Notice: Subject to any disclaimer, the term of this patent is extended or adjusted under 35 U.S.C. 154(b) by 35 days.

(21) Appl. No.: 13/124,862

(22) PCT Filed: Oct. 19, 2009

(86) PCT No.: PCT/US2009/061124  
§ 371 (c)(1),  
(2), (4) Date: Apr. 19, 2011

(87) PCT Pub. No.: WO2010/048067  
PCT Pub. Date: Apr. 29, 2010

(65) Prior Publication Data  
US 2011/0207086 A1    Aug. 25, 2011

Related U.S. Application Data

(60) Provisional application No. 61/107,400, filed on Oct. 22, 2008.

(51) Int. Cl.  
*A61K 6/083*     (2006.01)

(52) U.S. Cl. .................. 523/118; 523/115; 523/116

(58) Field of Classification Search .................. 523/115, 523/116, 118  
See application file for complete search history.

(56) References Cited

U.S. PATENT DOCUMENTS

| | | | |
|---|---|---|---|
| 3,018,262 A | 1/1962 | Schroeder | |
| 3,709,866 A | 1/1973 | Waller | |
| 3,860,556 A | 1/1975 | Taylor | |
| 4,259,075 A | 3/1981 | Yamauchi | |
| 4,298,738 A | 11/1981 | Lechtken | |
| 4,324,744 A | 4/1982 | Lechtken | |
| 4,356,296 A | 10/1982 | Griffith | |
| 4,385,109 A | 5/1983 | Lechtken | |
| 4,499,251 A | 2/1985 | Omura | |
| 4,503,169 A | 3/1985 | Randklev | |
| 4,518,756 A | 5/1985 | Yoshida | |
| 4,537,940 A | 8/1985 | Omura | |
| 4,539,382 A | 9/1985 | Omura | |
| 4,642,126 A | 2/1987 | Zador | |
| 4,648,843 A | 3/1987 | Mitra | |
| 4,652,274 A | 3/1987 | Boettcher | |
| 4,665,217 A | 5/1987 | Reiners | |
| 4,710,523 A | 12/1987 | Lechtken | |
| 4,737,593 A | 4/1988 | Ellrich | |
| 4,752,338 A | 6/1988 | Reiners | |
| 4,814,362 A * | 3/1989 | Billington et al. ............ 523/117 |
| 4,872,936 A | 10/1989 | Engelbrecht | |
| 4,962,163 A | 10/1990 | Hefner | |
| 5,026,902 A | 6/1991 | Fock | |
| 5,037,861 A | 8/1991 | Crivello | |
| 5,063,257 A | 11/1991 | Akahane | |
| 5,076,844 A | 12/1991 | Fock | |
| 5,130,347 A | 7/1992 | Mitra | |
| 5,154,762 A | 10/1992 | Mitra | |
| 5,227,413 A | 7/1993 | Mitra | |
| 5,367,002 A | 11/1994 | Huang | |
| 5,501,727 A | 3/1996 | Wang | |
| 5,520,725 A | 5/1996 | Kato | |
| 5,530,038 A | 6/1996 | Yamamoto | |
| 5,545,676 A | 8/1996 | Palazzotto | |
| 5,856,373 A | 1/1999 | Kaisaki | |
| 5,859,089 A | 1/1999 | Qian | |
| 5,871,360 A | 2/1999 | Kato | |
| 5,925,715 A | 7/1999 | Mitra | |
| 5,962,550 A | 10/1999 | Akahane | |
| 5,965,632 A | 10/1999 | Orlowski | |
| 5,998,499 A * | 12/1999 | Klee et al. ..................... 523/118 |
| 6,030,606 A | 2/2000 | Holmes | |
| 6,084,004 A | 7/2000 | Weinmann | |
| 6,147,137 A * | 11/2000 | Jia ................................. 523/118 |
| 6,187,833 B1 | 2/2001 | Oxman | |
| 6,187,836 B1 | 2/2001 | Oxman | |
| 6,245,828 B1 | 6/2001 | Weinmann | |
| 6,251,963 B1 | 6/2001 | Kohler | |
| 6,331,080 B1 | 12/2001 | Cole | |

(Continued)

FOREIGN PATENT DOCUMENTS

| EP | 0173567 | 3/1986 |
|---|---|---|
| EP | 0712622 | 9/1999 |

(Continued)

OTHER PUBLICATIONS

Inan, Preparation and Characterization of Novel UV-Curable Urethane Methacrylate Difunctional Monomers and Their Structure-Property Relationship, 1; Macromol. Chem. Phys. 2001, 2020 No. 4, pp. 532-540.  
International Search Report PCT/US2009/061124 Mar. 28, 2011; 4 pgs.  
Mathis et al., Properties of a New Glass Inonmer/Composite Resin Hybrid Restorative, Abstract No. 51; J. Dent. Res., 66:113 (1987).  
Greber et al; Darstellung und Polymerisation von ungesattigten 1,3,5-Triphenylbenzolderivaten; Journal Makromolekulare Chemie; 40, 1960; pp. 1-15.  
Levashova et al., The Effect of Substituents in the Aromatic Ring of Phenol on the Alkenylation of 3-Chloro-2-Chloromethyl-1-Propene, 1989, pp. 1319-1321.  
Lein et al., Host-Guest Complexation. 34. Bridged Hemispherands, J. Am. Chem. Soc., vol. 107, No. 2, 1985, pp. 448-455.  
ChemBlink 4,4'-Bis(2-hydroxyethoxy)biphenyl [printed from the internet on Apr. 11, 2012], <http://www.chemblink.com/products/20994-26-7.htm>, 2 pages.

*Primary Examiner* — James J Seidleck  
*Assistant Examiner* — Peter A Salamon  
(74) *Attorney, Agent, or Firm* — Carolyn A. Fischer

(57) ABSTRACT

Dental compositions and biphenyl di(meth)acrylate monomers are described. The dental compositions comprise at least one biphenyl di(meth)acrylate monomer comprising two aromatic rings connected with a C—C bond wherein the rings each comprise a substituent comprising a urethane moiety and a (meth)acrylate end group.

19 Claims, No Drawings

U.S. PATENT DOCUMENTS

| | | |
|---|---|---|
| 6,387,979 B1 | 5/2002 | Hino |
| 6,387,981 B1 | 5/2002 | Zhang |
| 6,444,725 B1 | 9/2002 | Trom |
| 6,458,868 B1 | 10/2002 | Okada |
| 6,528,555 B1 | 3/2003 | Nikutowski |
| 6,566,413 B1 | 5/2003 | Weinmann |
| 6,572,693 B1 | 6/2003 | Wu |
| 6,624,236 B1 | 9/2003 | Bissinger |
| 6,669,927 B2 | 12/2003 | Trom |
| 6,670,436 B2 | 12/2003 | Burgath |
| 6,730,156 B1 * | 5/2004 | Windisch et al. ............ 106/35 |
| 6,765,036 B2 | 7/2004 | Dede |
| 6,765,038 B2 | 7/2004 | Mitra |
| 6,779,656 B2 | 8/2004 | Klettke |
| 6,852,795 B2 | 2/2005 | Bissinger |
| 6,852,822 B1 | 2/2005 | Bissinger |
| 6,899,948 B2 | 5/2005 | Zhang |
| 6,982,288 B2 | 1/2006 | Mitra |
| 7,087,195 B2 | 8/2006 | Kawasaki |
| 7,090,721 B2 | 8/2006 | Craig |
| 7,090,722 B2 | 8/2006 | Budd |
| 7,156,911 B2 * | 1/2007 | Kangas et al. ............... 106/35 |
| 7,173,074 B2 | 2/2007 | Mitra |
| 7,241,437 B2 | 7/2007 | Davidson |
| 7,262,228 B2 | 8/2007 | Oxman |
| 7,393,882 B2 | 7/2008 | Wu |
| 7,888,400 B2 | 2/2011 | Abuelyaman |
| 2003/0114553 A1 | 6/2003 | Karim |
| 2004/0151691 A1 | 8/2004 | Oxman |
| 2004/0206932 A1 | 10/2004 | Abuelyaman |
| 2005/0100868 A1 | 5/2005 | Karim |
| 2005/0256223 A1 | 11/2005 | Kolb |
| 2007/0248927 A1 | 10/2007 | Luchterhandt |
| 2008/0009416 A1 * | 1/2008 | Selph et al. ................ 504/156 |
| 2008/0076745 A1 * | 3/2008 | Endermann et al. ......... 514/183 |
| 2008/0221291 A1 * | 9/2008 | Invie et al. ................. 526/313 |
| 2010/0003501 A1 | 1/2010 | Liu |
| 2010/0021869 A1 | 1/2010 | Abuelyaman |
| 2010/0197824 A1 | 8/2010 | Bissinger |
| 2011/0053116 A1 | 3/2011 | Hecht |

FOREIGN PATENT DOCUMENTS

| | | |
|---|---|---|
| JP | 60-197711 | 10/1985 |
| JP | 01213211 | 8/1989 |
| JP | 04001762 | 1/1992 |
| JP | 3021152 A * | 7/1993 |
| JP | 05170705 | 7/1993 |
| JP | 07-247306 | 9/1995 |
| JP | 08-113616 | 5/1996 |
| JP | 1213211 A * | 8/1998 |
| JP | 2008247755 A * | 10/2008 |
| WO | WO 2006/007286 | 1/2006 |
| WO | WO 2006/093075 | 9/2006 |
| WO | WO 2007/001811 | 1/2007 |
| WO | WO 2008/120573 | 10/2008 |
| WO | WO 2010/027676 | 3/2010 |

* cited by examiner

DENTAL COMPOSITION COMPRISING BIPHENYL DI(METH)ACRYLATE MONOMER COMPRISING URETHANE MOIETIES

CROSS REFERENCE TO RELATED APPLICATIONS

This application is a national stage filing under 35 U.S.C. 371 of PCT/US2009/061124, filed Oct. 19, 2009, which claims priority to U.S. Provisional Application Ser. No. 61/107,400 filed Oct. 22, 2008, the disclosure of which is incorporated by reference in its entirety herein.

BACKGROUND

Various aromatic di(meth)acrylate monomers have been employed in hardenable dental compositions. (See for example U.S. Pat. No. 3,709,866; U.S. Pat. No. 3,860,556; and WO 2008/082881).

Industry would find advantage in dental compositions comprising alternative aromatic di(meth)acrylate monomers, particularly those dental compositions that exhibit improved (e.g. staining resistance) properties.

SUMMARY

In some embodiments, hardenable dental compositions and dental articles comprising hardened (i.e. cured) compositions are described. The composition comprises at least one biphenyl monomer comprising two aromatic rings connected with a C—C bond wherein the rings each comprise a substituent comprising a urethane moiety and a (meth)acrylate end group.

In one embodiment, the hardenable dental composition comprises at least one biphenyl monomer comprising two aromatic rings connected with a C—C bond wherein each ring comprises a substituent comprising a urethane moiety and a (meth)acrylate end group; at least one other ethylenically unsaturated monomer that is a liquid at 25° C.; and at least one inorganic nanoparticle filler.

In other embodiments, biphenyl di(meth)acrylate monomers are described having the general structure

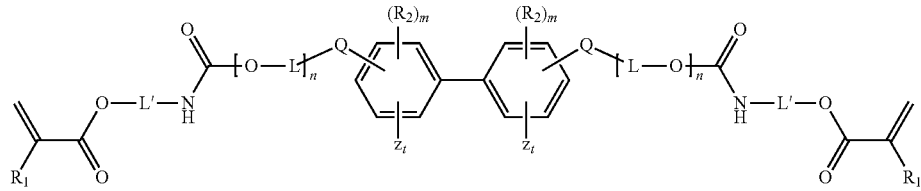

wherein $R_2$ is independently a halogen or a $C_1$ to $C_4$ alkyl group;
m ranges from 0 to 4;
z is an aromatic ring;
t is independently 0 or 1;
Q is independently O or S;
L is independently a $C_2$ to $C_{12}$ alkylene group optionally substituted with one or more hydroxyl groups;
n independently ranges from 0 to 10;
L' is independently a $C_2$ to $C_{12}$ alkylene group; and
$R_1$ is independently H or methyl.

In some embodiments, m is 0 and/or t is 0 and/or Q is oxygen. Further, n is 1 and L is $C_2$ or $C_3$.

DETAILED DESCRIPTION

As used herein, "dental composition" refers to an unfilled or filled (e.g. a composite) material (e.g., a dental or orthodontic material) capable of adhering or being bonded to an oral surface. Dental compositions include, for example, adhesives (e.g., dental and/or orthodontic adhesives), cements (e.g., glass ionomer cements, resin-modified glass ionomer cements, and/or orthodontic cements), primers (e.g., orthodontic primers), restoratives such as dental fillings, liners, sealants (e.g., orthodontic sealants), and coatings. Oftentimes a dental composition can be used to bond a dental article to a tooth structure.

As used herein, "dental article" refers to an article that can be adhered (e.g., bonded) to a tooth structure. Dental articles include, for example, crowns, bridges, veneers, inlays, onlays, fillings, orthodontic appliances and devices, and prostheses (e.g., partial or full dentures).

As used herein, "orthodontic appliance" refers to any device intended to be bonded to a tooth structure, including, but not limited to, orthodontic brackets, buccal tubes, lingual retainers, orthodontic bands, bite openers, buttons, and cleats. The appliance has a base for receiving adhesive and it can be a flange made of metal, plastic, ceramic, or combinations thereof. Alternatively, the base can be a custom base formed from cured adhesive layer(s) (i.e., single or multi-layer adhesives).

As used herein, an "oral surface" refers to a soft or hard surface in the oral environment. Hard surfaces typically include tooth structure including, for example, natural and artificial tooth surfaces, bone, tooth models, and the like.

As used herein, "hardenable" is descriptive of a material or composition that can be cured (e.g., polymerized or crosslinked) by heating to induce polymerization and/or crosslinking; irradiating to induce polymerization and/or crosslinking; and/or by mixing one or more components to induce polymerization and/or crosslinking. "Mixing" can be performed, for example, by combining two or more parts and mixing to form a homogeneous composition. Alternatively, two or more parts can be provided as separate layers that intermix (e.g., spontaneously or upon application of shear stress) at the interface to initiate polymerization.

As used herein, "hardened" refers to a material or composition that has been cured (e.g., polymerized or crosslinked) or solidified.

As used herein, "hardener" refers to something that initiates hardening of a resin. A hardener may include, for example, a polymerization initiator system, a photoinitiator system, and/or a redox initiator system.

As used herein, the term "(meth)acrylate" is a shorthand reference to acrylate, methacrylate, or combinations thereof; "(meth)acrylic" is a shorthand reference to acrylic, methacrylic, or combinations thereof; and "(meth)acryloyl" is a shorthand reference to acryloyl, methacryloyl, or combinations thereof. As used herein, "(meth)acryloyl-containing compounds" are compounds that include, among other things, a (meth)acrylate moiety, a (meth)acrylamide moiety, or combinations thereof.

As used herein, "a," "an," "the," "at least one," and "one or more" are used interchangeably.

Also herein, the recitations of numerical ranges by endpoints include all numbers subsumed within that range (e.g., 1 to 5 includes 1, 1.5, 2, 2.75, 3, 3.80, 4, 5, etc.).

The dental compositions described herein comprise at least one biphenyl monomer. Such monomers comprise a biphenyl core structure wherein the two aromatic (e.g. phenyl) groups are not fused, but joined by a C—C bond. The biphenyl monomers described herein do not contain any groups between the aromatic (e.g., phenyl) groups. However, each of the aromatic (e.g. phenyl) groups comprise at least one (e.g. single) substituent comprising a urethane moiety and a polymerizable (meth)acrylate or thio(meth)acrylate (e.g. end) group.

Such biphenyl di(meth)acrylate monomers typically have the general structure

M-C—Ar—Ar—C-M (II)

wherein Ar is independently an aromatic group (e.g., phenyl or naphthyl); C represents one or more connecting atoms, and each M is —C(O)—NH—$(CH_2)_m$—O—C(O)—C($R_1$)=$CH_2$, wherein m is at least 1 and $R_1$ is H or methyl.

In some embodiments, at least one and typically both of the polymerizable (meth)acrylate group containing substituents are attached to the Ar group at an ortho position. The substituent comprises a urethane moiety provided between the Ar (e.g. phenyl) group and the (meth)acrylate group. In some embodiments, the substituents further comprise an alkoxy linking group, wherein the carbon atoms are optionally substituted with hydroxyl, between the aromatic (e.g., phenyl) group and the (meth)acrylate group. The substituent (i.e. comprising the urethane moiety and the (meth)acrylate group) typically has a molecular (e.g. atomic) weight of less than 1000 g/mole. In some embodiments, the substituent preferably has a molecular (e.g. atomic) weight of less than 500 g/mole, less than 400 g/mole, or less than 300 g/mole. The linking group is preferably a $C_2$-$C_3$ alkoxy group optionally substituted with one or more hydroxyl groups.

In some embodiments, the biphenyl di(meth)acrylate monomer has the general structure z is an aromatic ring;
t is independently 0 or 1;
Q is independently O or S;
L is independently a $C_2$ to $C_{12}$ alkylene group optionally substituted with one or more hydroxyl groups;
n independently ranges from 0 to 10;
L' is independently a $C_2$ to $C_{12}$ alkylene group; and
$R_1$ is independently H or methyl.

In some embodiments, m is 0 and/or t is 0. In preferred embodiments, the aromatic rings are phenyl rings that comprise no other substituents other than the (meth)acrylate group containing substituent. Thus, m and t are 0. Q is preferably oxygen. In some embodiments, n ranges from 0 to 10. Further, L is preferably a $C_2$ to $C_6$ alkylene group optionally substituted with one or more hydroxyl groups. Although n can be 0, n is typically 1 or 2. In some embodiments, L is preferably $C_2$ or $C_3$ or a hydroxyl substituted $C_2$ or $C_3$. L' is preferably a $C_2$ to $C_6$ alkylene groups and more preferably $C_2$ or $C_3$. However, other biphenyl core structures and substituents may be preferred when the biphenyl di(meth)acrylate monomer is utilized in other (e.g. non-dental) compositions. In some embodiments, z is an aromatic ring fused to a phenyl group thereby forming a binaphthyl core structure. In other embodiments, z is an aromatic ring connected to a phenyl group by a C—C bond, thereby forming a multiple biphenyl core structure.

Suitable biphenyl di(meth)acrylate monomers having such general structure are depicted as follows:

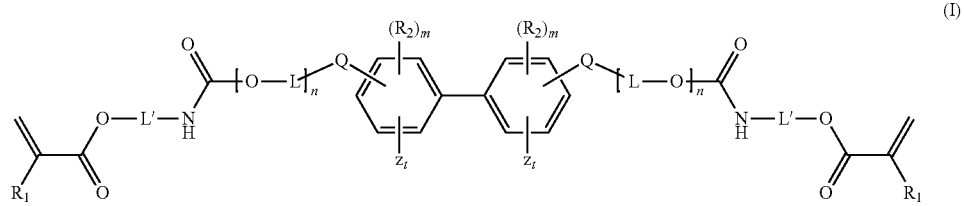

(I)

wherein $R_2$ is independently a halogen such as Br or a (e.g. $C_1$ to $C_4$) alkyl group;
m ranges from 0 to 4;

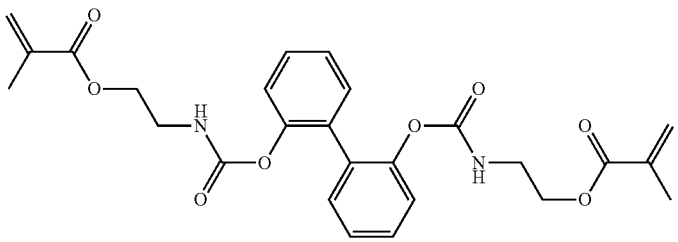

2-{2'-[2-(methacryloyloxy)ethylcarbamoyloxy]biphenyl-2-yloxycarbonylamino}ethyl methacrylate (III)

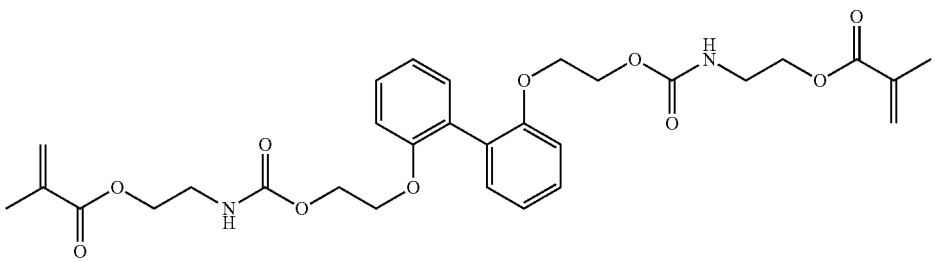

2-[2-(2'-{2-[2-(methacryloyloxy)ethylcarbamoyloxy]ethoxy}biphenyl-2-yloxy)ethoxycarbonylamino]ethyl methacrylate (IV)

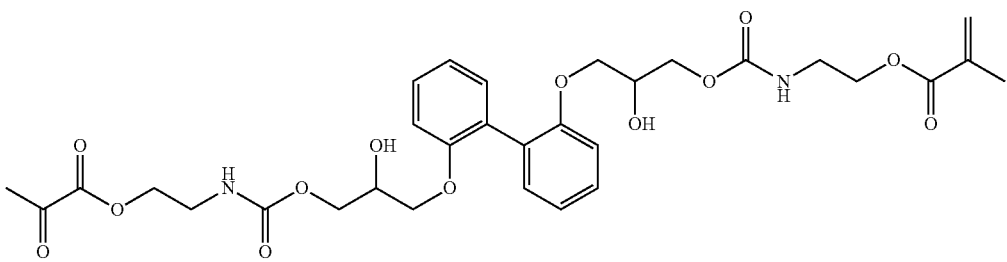

2-[2-hydroxy-3-(2'-{2-hydroxy-3-[2-(methacryloyloxy)ethylcarbamoyloxy]propoxy}biphenyl-2-yloxy)propoxycarbonylamino]ethyl methacrylate (V)

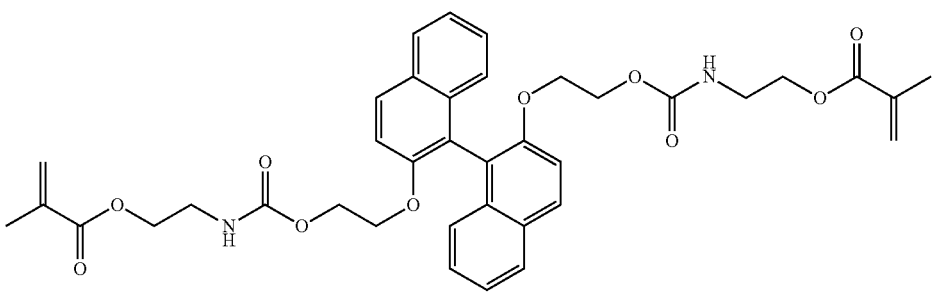

2-[2-(2'-{2-[2-(methacryloyloxy)ethylcarbamoyloxy]ethoxy}[1,1']binaphthalenyl-2-yloxy)ethoxycarbonylamino]ethyl methacrylate (VI)

-continued

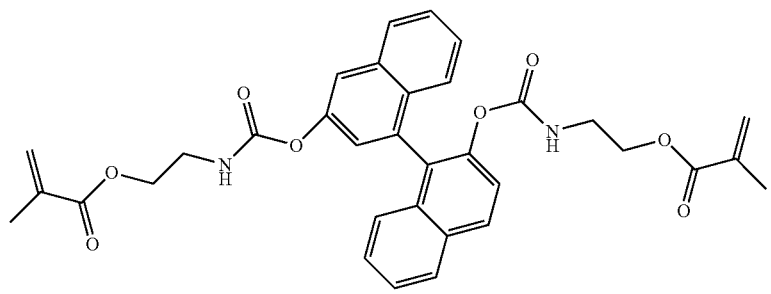

2-{2'-[2-(methacryloyloxy)ethylcarbamoyloxy][1,1']binaphthalenyl-2-yloxycarbonylamino}ethyl methacrylate (VII)

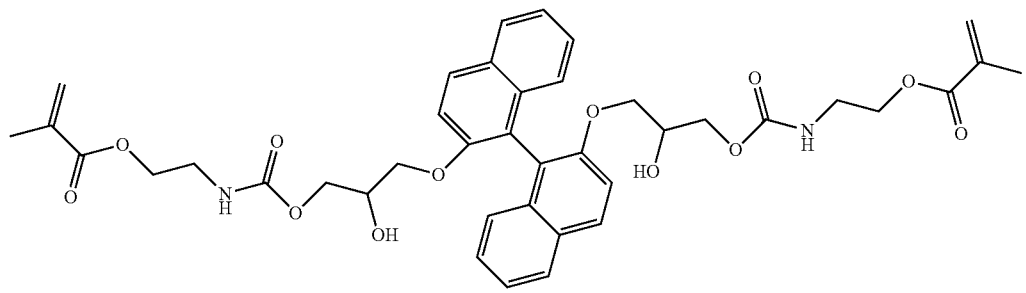

2-[2-hydroxy-3-(2'-{2-hydroxy-3-[2-(methacryloyloxy)ethylcarbamoyloxy]propoxy}[1,1']binaphthalenyl-2-yloxy)propoxycarbonylamino]ethyl methacrylate (VIII)

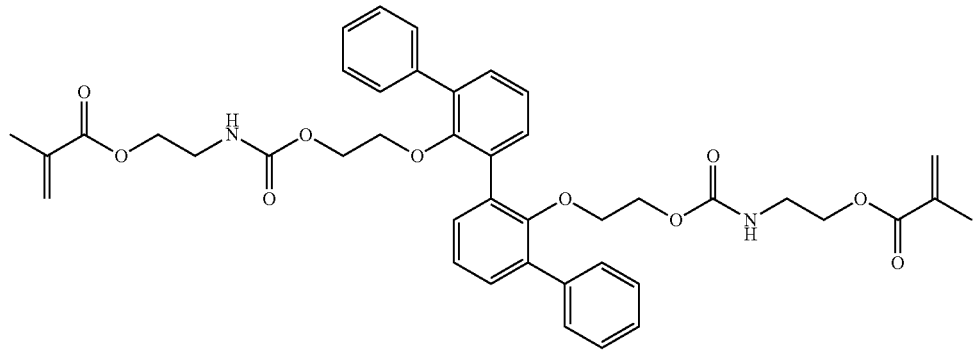

2-[2-(2''-{2-[2-(methacryloyloxy)ethylcarbamoyloxy]ethoxy}[1,1';3',1'';3'',1''']quaterphenyl-2'-yloxy)ethoxycarbonylamino]ethyl methacrylate (IX)

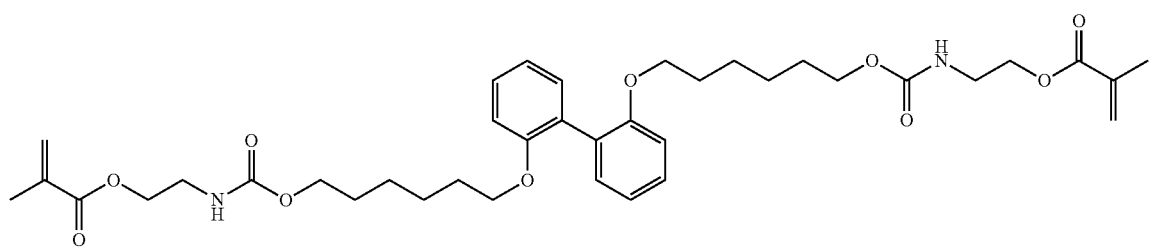

2-[6-(2'-{6-[2-(methacryloyloxy)ethylcarbamoyloxy]hexyloxy}biphenyl-2-yloxy)hexyloxycarbonylamino]ethyl methacrylate (X)

Biphenyl di(meth)acrylate monomers in accordance with structure IV can be prepared by reaction of biphenyl-2,2'-diol (i.e., 2,2'-dihydroxybiphenyl) with ethylene carbonate to produce 2-[2'-(2-hydroxyethoxy)biphenyl-2-yloxy]ethanol which is then reacted with isocyanotoethyl methacrylate. Each of the binaphthyl molecules (e.g. structures VI-VIII) can be prepared in an analogous synthesis using 2,2'-dihydroxy-1,1'-binaphthyl as the starting material rather than 2,2'-dihydroxybiphenyl. Other syntheses could be employed by one of ordinary skill in the art.

The biphenyl di(meth)acrylate monomer typically comprises a major amount of ortho (meth)acrylate substituents (i.e. at least 50%, 60%, 70%, 80%, 90%, or 95% of the substituents of the biphenyl di(meth)acrylate monomer). It is surmised that as the number of meta- and particularly para-substituents increases, the viscosity of the monomer can increase and the solubility of the monomer can decrease.

In some embodiments, such as when the dental composition is employed as a dental restorative (e.g. dental filling or crown) or an orthodontic adhesive, the dental composition typically comprises appreciable amounts of (e.g. nanoparticle) filler. Such compositions preferably include at least 40 wt-%, more preferably at least 45 wt-%, and most preferably at least 50 wt-% filler, based on the total weight of the composition. In some embodiments the total amount of filler is at most 90 wt-%, preferably at most 80 wt-%, and more preferably at most 75 wt-% filler.

In such dental compositions comprising appreciable amounts of filler, the one or more biphenyl di(meth)acrylate monomers are typically present in an amount totaling at least 5 wt-%, 6 wt-%, 7 wt-%, 8 wt-%, 9 wt-%, or 10 wt-%, based on the total weight of the composition. The concentration of biphenyl di(meth)acrylate monomers is generally no greater than about 60 wt-%. In some embodiments the total amount of biphenyl di(meth)acrylate monomer(s) is at most 40 wt-%, preferably at most 30 wt-%, and more preferably at most 25 wt-%.

Preferred dental compositions exhibit at least comparable properties to commercially available hardenable dental compositions (as determined by the test methods described in the examples). In some embodiments, the pre-cure hardness of filler-containing dental compositions is at least 500 g or 1000 g at 28° C. Further the flexural strength is typically at least 50 MPa or 100 MPa. Further, the flexural modulus is typically at least 5000 MPa.

In some preferred embodiments, such as set forth in the examples, the dental compositions described herein are hardened to dental articles that exhibit improved staining resistance properties as measured by, $\Delta E^*$, which indicates the total color change in a 3-dimensional color space after conditioning in a solution known to cause staining. In one embodiment, the hardened dental composition exhibits a staining resistance, $\Delta E^*$, of less than 8, 7, 6, or 5 after 3 days conditioning in coffee solution according to the Staining Test (i.e. described in the examples). In other embodiments, the hardened dental composition exhibits improved staining resistance when conditioned in a mustard/ketchup or red wine solution.

For embodiments wherein the dental composition is employed as an adhesive or cement, the amount of biphenyl di(meth)acrylate monomer(s) can be considerably higher. Provided that the biphenyl di(meth)acrylate monomer is a liquid at 25° C., the dental compositions may contain one or more biphenyl di(meth)acrylate monomer(s) as the sole polymerizable monomer component.

Dental compositions suitable for use as dental adhesives can also include filler in amount of at least 1 wt-%, 2 wt-%, 3 wt-%, 4 wt-%, or 5 wt-% based on the total weight of the composition. For such embodiments, the total concentration of filler is at most 40 wt-%, preferably at most 20 wt-%, and more preferably at most 15 wt-% filler, based on the total weight of the composition.

Fillers may be selected from one or more of a wide variety of materials suitable for incorporation in compositions used for dental applications, such as fillers currently used in dental restorative compositions, and the like.

The filler can be an inorganic material. It can also be a crosslinked organic material that is insoluble in the polymerizable resin, and is optionally filled with inorganic filler. The filler is generally non-toxic and suitable for use in the mouth. The filler can be radiopaque, radiolucent, or nonradiopaque. Fillers as used in dental applications are typically ceramic in nature.

Non-acid-reactive inorganic filler particles include quartz (i.e., silica), submicron silica, zirconia, submicron zirconia, and non-vitreous microparticles of the type described in U.S. Pat. No. 4,503,169 (Randklev).

The filler can also be an acid-reactive filler. Suitable acid-reactive fillers include metal oxides, glasses, and metal salts. Typical metal oxides include barium oxide, calcium oxide, magnesium oxide, and zinc oxide. Typical glasses include borate glasses, phosphate glasses, and fluoroaluminosilicate ("FAS") glasses. The FAS glass typically contains sufficient elutable cations so that a hardened dental composition will form when the glass is mixed with the components of the hardenable composition. The glass also typically contains sufficient elutable fluoride ions so that the hardened composition will have cariostatic properties. The glass can be made from a melt containing fluoride, alumina, and other glass-forming ingredients using techniques familiar to those skilled in the FAS glassmaking art. The FAS glass typically is in the form of particles that are sufficiently finely divided so that they can conveniently be mixed with the other cement components and will perform well when the resulting mixture is used in the mouth.

Generally, the average particle size (typically, diameter) for the FAS glass is no greater than 12 micrometers, typically no greater than 10 micrometers, and more typically no greater than 5 micrometers as measured using, for example, a sedimentation particle size analyzer. Suitable FAS glasses will be familiar to those skilled in the art, and are available from a wide variety of commercial sources, and many are found in currently available glass ionomer cements such as those commercially available under the trade designations VITREMER, VITREBOND, RELY X LUTING CEMENT, RELY X LUTING PLUS CEMENT, PHOTAC-FIL QUICK, KETAC-MOLAR, and KETAC-FIL PLUS (3M ESPE Dental Products, St. Paul, Minn.), FUJI II LC and FUJI IX (G-C Dental Industrial Corp., Tokyo, Japan) and CHEMFIL Superior (Dentsply International, York, Pa.). Mixtures of fillers can be used if desired.

Other suitable fillers are disclosed in U.S. Pat. No. 6,387,981 (Zhang et al.) and U.S. Pat. No. 6,572,693 (Wu et al.) as well as PCT International Publication Nos. WO 01/30305 (Zhang et al.), WO 01/30306 (Windisch et al.), WO 01/30307 (Zhang et al.), and WO 03/063804 (Wu et al.). Filler components described in these references include nanosized silica particles, nanosized metal oxide particles, and combinations thereof. Nanofillers are also described in U.S. Pat. No. 7,090,721 (Craig et al.), U.S. Pat. No. 7,090,722 (Budd et al.) and U.S. Pat. No. 7,156,911; and U.S. Patent Application Publication No. 2005/0256223 A1 (Kolb et al.).

Examples of suitable organic filler particles include filled or unfilled pulverized polycarbonates, polyepoxides, poly (meth)acrylates and the like. Commonly employed dental filler particles are quartz, submicron silica, and non-vitreous microparticles of the type described in U.S. Pat. No. 4,503,169 (Randklev).

Mixtures of these fillers can also be used, as well as combination fillers made from organic and inorganic materials.

Fillers may be either particulate or fibrous in nature. Particulate fillers may generally be defined as having a length to width ratio, or aspect ratio, of 20:1 or less, and more commonly 10:1 or less. Fibers can be defined as having aspect ratios greater than 20:1, or more commonly greater than 100:1. The shape of the particles can vary, ranging from spherical to ellipsoidal, or more planar such as flakes or discs. The macroscopic properties can be highly dependent on the shape of the filler particles, in particular the uniformity of the shape.

Micron-size particles are very effective for improving post-cure wear properties. In contrast, nanoscopic fillers are commonly used as viscosity and thixotropy modifiers. Due to their small size, high surface area, and associated hydrogen bonding, these materials are known to assemble into aggregated networks.

In some embodiments, the dental composition preferably comprise a nanoscopic particulate filler (i.e., a filler that comprises nanoparticles) having an average primary particle size of less than about 0.100 micrometers (i.e., microns), and more preferably less than 0.075 microns. As used herein, the term "primary particle size" refers to the size of a non-associated single particle. The average primary particle size can be determined by cutting a thin sample of hardened dental composition and measuring the particle diameter of about 50-100 particles using a transmission electron micrograph at a magnification of 300,000 and calculating the average. The filler can have a unimodal or polymodal (e.g., bimodal) particle size distribution. The nanoscopic particulate material typically has an average primary particle size of at least about 2 nanometers (nm), and preferably at least about 7 nm. Preferably, the nanoscopic particulate material has an average primary particle size of no greater than about 50 nm, and more preferably no greater than about 20 nm in size. The average surface area of such a filler is preferably at least about 20 square meters per gram ($m^2/g$), more preferably, at least about 50 $m^2/g$, and most preferably, at least about 100 $m^2/g$.

In some preferred embodiments, the dental composition comprises silica nanoparticles. Suitable nano-sized silicas are commercially available from Nalco Chemical Co. (Naperville, Ill.) under the product designation NALCO COLLOIDAL SILICAS. For example, preferred silica particles can be obtained from using NALCO products 1040, 1042, 1050, 1060, 2327 and 2329.

Silica particles are preferably made from an aqueous colloidal dispersion of silica (i.e., a sol or aquasol). The colloidal silica is typically in the concentration of about 1 to 50 weight percent in the silica sol. Colloidal silica sols which can be used in preparing the fillers of the invention are available commercially having different colloid sizes, see Surface & Colloid Science, Vol. 6, ed. Matijevic, E., Wiley Interscience, 1973. Preferred silica sols for use making the fillers of the invention are those which are supplied as a dispersion of amorphous silica in an aqueous medium (such as the Nalco colloidal silicas made by Nalco Chemical Company) and those which are low in sodium concentration and can be acidified by admixture with a suitable acid (e.g. Ludox colloidal silica made by E. I. Dupont de Nemours & Co. or Nalco 2326 from Nalco Chemical Co.).

Preferably, the silica particles in the sol have an average particle diameter of about 5-100 nm, more preferably 10-50 nm, and most preferably 12-40 nm. A particularly preferred silica sol is NALCO 1041.

In some embodiments, the dental composition comprises zirconia nanoparticles. Suitable nano-sized zirconia nanoparticles can be prepared using hydrothermal technology as described in U.S. Pat. No. 7,241,437 (Davidson et al.).

In some embodiments, lower refractive index (e.g. silica) nanoparticles are employed in combination with high refractive index (e.g. zirconia) nanoparticles in order to index match (refractive index within 0.02) the filler to the refractive index of the polymerizable resin.

In some embodiments, the nanoparticles are in the form of nanoclusters, i.e. a group of two or more particles associated by relatively weak intermolecular forces that cause the particles to clump together, even when dispersed in a hardenable resin. Preferred nanoclusters can comprise a substantially amorphous cluster of non-heavy (e.g. silica) particles, and amorphous heavy metal oxide (i.e. having an atomic number greater than 28) particles such as zirconia. The particles of the nanocluster preferably have an average diameter of less than about 100 nm. Suitable nanocluster fillers are described in U.S. Pat. No. 6,730,156 (Windisch et al.); incorporated herein by reference.

In some preferred embodiments, the dental composition comprises nanoparticles and/or nanoclusters surface treated with an organometallic coupling agent to enhance the bond between the filler and the resin. The organometallic coupling agent may be functionalized with reactive curing groups, such as acrylates, methacrylates, vinyl groups and the like.

Suitable copolymerizable organometallic compounds may have the general formula:

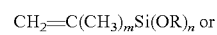

$CH_2=C(CH_3)_m Si(OR)_n$ or

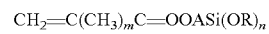

$CH_2=C(CH_3)_m C=OOASi(OR)_n$ wherein m is 0 or 1,
R is an alkyl group having 1 to 4 carbon atoms,
A is a divalent organic linking group, and
n is from 1 to 3.

Preferred coupling agents include gamma-methacryloxypropyltrimethoxysilane, gamma-mercaptopropyltriethoxysilane, gamma-aminopropyltrimethoxysilane, and the like.

In some embodiments, a combination of surface modifying agents can be useful, wherein at least one of the agents has a functional group co-polymerizable with a hardenable resin. Other surface modifying agents which do not generally react with hardenable resins can be included to enhance dispersibility or rheological properties. Examples of silanes of this type include, for example, aryl polyethers, alkyl, hydroxy alkyl, hydroxy aryl, or amino alkyl functional silanes.

The surface modification can be done either subsequent to mixing with the monomers or after mixing. It is typically preferred to combine the organosilane surface treatment compounds with nanoparticles before incorporation into the resin. The required amount of surface modifier is dependant upon several factors such as particle size, particle type, modifier molecular wt, and modifier type. In general it is preferred that approximately a monolayer of modifier is attached to the surface of the particle.

The surface modified nanoparticles can be substantially fully condensed. Fully condensed nanoparticles (with the exception of silica) typically have a degree of crystallinity (measured as isolated metal oxide particles) greater than 55%, preferably greater than 60%, and more preferably greater than 70%. For example, the degree of crystallinity can range up to about 86% or greater. The degree of crystallinity can be determined by X-ray diffraction techniques. Condensed crystalline (e.g. zirconia) nanoparticles have a high refractive index whereas amorphous nanoparticles typically have a lower refractive index.

In addition to the biphenyl di(meth)acrylate monomer described herein, the hardenable component of the dental composition can include a wide variety of chemistries, such as ethylenically unsaturated compounds (with or without acid functionality), epoxy (oxirane) resins, vinyl ethers, (e.g. photopolymerization) initiator systems, redox cure systems, glass ionomer cements, polyethers, polysiloxanes, and the like.

In certain embodiments, the compositions are photopolymerizable, i.e., the compositions contain a photoinitiator (i.e., a photoinitiator system) that upon irradiation with actinic radiation initiates the polymerization (or hardening) of the composition. Such photopolymerizable compositions can be free radically polymerizable or cationically polymerizable. In other embodiments, the compositions are chemically hardenable, i.e., the compositions contain a chemical initiator (i.e., initiator system) that can polymerize, cure, or otherwise harden the composition without dependence on irradiation with actinic radiation. Such chemically hardenable compositions are sometimes referred to as "self-cure" compositions and may include glass ionomer cements (e.g., conventional and resin-modified glass ionomer cements), redox cure systems, and combinations thereof.

Suitable photopolymerizable components that can be used in the dental compositions of the present invention include, for example, epoxy resins (which contain cationically active epoxy groups), vinyl ether resins (which contain cationically active vinyl ether groups), ethylenically unsaturated compounds (which contain free radically active unsaturated groups, e.g., acrylates and methacrylates), and combinations thereof. Also suitable are polymerizable materials that contain both a cationically active functional group and a free radically active functional group in a single compound. Examples include epoxy-functional acrylates, epoxy-functional methacrylates, and combinations thereof.

The (e.g., photopolymerizable) dental compositions may include compounds having free radically active functional groups that may include monomers, oligomers, and polymers having one or more ethylenically unsaturated group. Suitable compounds contain at least one ethylenically unsaturated bond and are capable of undergoing addition polymerization. Examples of useful ethylenically unsaturated compounds include acrylic acid esters, methacrylic acid esters, hydroxy-functional acrylic acid esters, hydroxy-functional methacrylic acid esters, and combinations thereof. Such free radically polymerizable compounds include mono-, di- or poly-(meth)acrylates (i.e., acrylates and methacrylates) such as, methyl (meth)acrylate, ethyl (meth)acrylate, isopropyl (meth)acrylate, n-hexyl (meth)acrylate, stearyl (meth)acrylate, allyl (meth)acrylate, glycerol tri(meth)acrylate, ethyleneglycol di(meth)acrylate, diethyleneglycol di(meth)acrylate, triethyleneglycol di(meth)acrylate, 1,3-propanediol di(meth)acrylate, trimethylolpropane tri(meth)acrylate, 1,2,4-butanetriol tri(meth)acrylate, 1,4-cyclohexanediol di(meth)acrylate, pentaerythritol tetra(meth)acrylate, sorbitol hex(meth)acrylate, tetrahydrofurfuryl (meth)acrylate, bis[1-(2-acryloxy)]-p-ethoxyphenyldimethylmethane, bis[1-(3-acryloxy-2-hydroxy)]-p-propoxyphenyldimethylmethane, ethoxylated bisphenolA di(meth)acrylate, and trishydroxyethyl-isocyanurate tri(meth)acrylate; (meth)acrylamides (i.e., acrylamides and methacrylamides) such as (meth)acrylamide, methylene bis-(meth)acrylamide, and diacetone (meth)acrylamide; urethane (meth)acrylates; the bis-(meth)acrylates of polyethylene glycols (preferably of molecular weight 200-500), copolymerizable mixtures of acrylated monomers such as those in U.S. Pat. No. 4,652,274 (Boettcher et al.), acrylated oligomers such as those of U.S. Pat. No. 4,642,126 (Zador et al.), and poly(ethylenically unsaturated) carbamoyl isocyanurates such as those disclosed in U.S. Pat. No. 4,648,843 (Mitra); and vinyl compounds such as styrene, diallyl phthalate, divinyl succinate, divinyl adipate and divinyl phthalate. Other suitable free radically polymerizable compounds include siloxane-functional (meth)acrylates as disclosed, for example, in PCT International Publication Nos. WO 00/38619 (Guggenberger et al.), WO 01/92271 (Weinmann et al.), WO 01/07444 (Guggenberger et al.), and WO 00/42092 (Guggenberger et al.); and fluoropolymer-functional (meth)acrylates as disclosed, for example, in U.S. Pat. No. 5,076,844 (Fock et al.) and U.S. Pat. No. 4,356,296 (Griffith et al.) and European Pat. Application Publication Nos. EP 0373 384 (Wagenknecht et al.), EP 0201 031 (Reiners et al.), and EP 0201 778 (Reiners et al.). Mixtures of two or more free radically polymerizable compounds can be used if desired.

The hardenable dental composition may also contain hydroxyl groups and ethylenically unsaturated groups in a single molecule. Examples of such materials include hydroxyalkyl (meth)acrylates, such as 2-hydroxyethyl (meth)acrylate and 2-hydroxypropyl (meth)acrylate; glycerol mono- or di-(meth)acrylate; trimethylolpropane mono- or di-(meth)acrylate; pentaerythritol mono-, di-, and tri-(meth)acrylate; sorbitol mono-, di-, tri-, tetra-, or penta-(meth)acrylate; and 2,2-bis[4-(2-hydroxy-3-ethacryloxypropoxy)phenyl]propane (bisGMA). Suitable ethylenically unsaturated compounds are also available from a wide variety of commercial sources, such as Sigma-Aldrich, St. Louis. Mixtures of ethylenically unsaturated compounds can be used if desired.

In certain embodiments hardenable components can include PEGDMA (polyethyleneglycol dimethacrylate having a molecular weight of approximately 400), bisGMA, UDMA (urethane dimethacrylate), GDMA (glycerol dimethacrylate), TEGDMA (triethyleneglycol dimethacrylate), bisEMA6 as described in U.S. Pat. No. 6,030,606 (Holmes), and NPGDMA (neopentylglycol dimethacrylate). Various combinations of the hardenable components can be used if desired.

In certain embodiments hardenable components can include one or more polymerizable hybrid compounds. Exemplary polymerizable hybrid compounds include, for example, compounds having at least one cyclic allylic sulfide group and at least one (meth)acryloyl group as described, for example, in PCT International Publication No. WO 2006/122081 A1 (Abuelyaman et al.). In some embodiments, polymerizable hybrid compounds can be included in dental compositions that, upon hardening, exhibit low shrinkage along with good mechanical properties.

In some embodiments, it is preferred to combine the biphenyl di(meth)acrylate monomer(s) with at least one other (meth)acrylate monomer, i.e. different than the biphenyl di(meth)acrylate monomer. For embodiments wherein the biphenyl di(meth)acrylate monomer is a solid at ambient temperature, it is typically preferred to dissolve biphenyl di(meth)acrylate monomer in a hardenable component such as an ethylenically unsaturated (e.g. meth)acrylate) monomer that is a liquid at ambient temperature (25° C.) such as TEGDMA, 2,2,-bis-4-(3-hydroxy-propoxy-phenyl)propane dimethacrylate (Procrylate), diurethane di(meth)acrylates, and mixtures thereof.

The concentration of other (meth)acrylate monomers can be at least 5 wt-%, 6 wt-%, 7 wt-%, 8 wt-%, 9 wt-%, or 10 wt-%, based on the total weight of the composition. For embodiments, wherein the dental composition comprises appreciable amounts of filler, the concentration of other monomer(s) is generally no greater than about 60 wt-%. The total amount of other monomer(s) is typically at most 40 wt-%, preferably at most 30-wt-%, and more preferably at most 25 wt-%. However, when the composition comprises little or no filler, the concentration of other monomer(s) can be considerably higher (e.g. up to about 90 wt-%).

The compositions of the present invention may include one or more hardenable components in the form of ethylenically unsaturated compounds with acid functionality, thereby forming hardenable compositions.

As used herein, ethylenically unsaturated compounds with acid functionality is meant to include monomers, oligomers, and polymers having ethylenic unsaturation and acid and/or acid-precursor functionality. Acid-precursor functionalities include, for example, anhydrides, acid halides, and pyrophosphates. The acid functionality can include carboxylic acid functionality, phosphoric acid functionality, phosphonic acid functionality, sulfonic acid functionality, or combinations thereof.

Ethylenically unsaturated compounds with acid functionality include, for example, $\alpha,\beta$-unsaturated acidic compounds such as glycerol phosphate mono(meth)acrylates, glycerol phosphate di(meth)acrylates, hydroxyethyl (meth)acrylate (e.g., HEMA) phosphates, bis((meth)acryloxyethyl) phosphate, ((meth)acryloxypropyl) phosphate, bis((meth)acryloxypropyl) phosphate, bis((meth)acryloxy)propyloxy phosphate, (meth)acryloxyhexyl phosphate, bis((meth)acryloxyhexyl) phosphate, (meth)acryloxyoctyl phosphate, bis((meth)acryloxyoctyl) phosphate, (meth)acryloxydecyl phosphate, bis((meth)acryloxydecyl) phosphate, caprolactone methacrylate phosphate, citric acid di- or tri-methacrylates, poly(meth)acrylated oligomaleic acid, poly(meth)acrylated polymaleic acid, poly(meth)acrylated poly(meth)acrylic acid, poly(meth)acrylated polycarboxyl-polyphosphonic acid, poly(meth)acrylated polychlorophosphoric acid, poly(meth)acrylated polysulfonate, poly(meth)acrylated polyboric acid, and the like, may be used as components in the hardenable component system. Also monomers, oligomers, and polymers of unsaturated carbonic acids such as (meth)acrylic acids, aromatic (meth)acrylated acids (e.g., methacrylated trimellitic acids), and anhydrides thereof can be used. The dental compositions can include an ethylenically unsaturated compound with acid functionality having at least one P—OH moiety.

Certain of these compounds are obtained, for example, as reaction products between isocyanatoalkyl (meth)acrylates and carboxylic acids. Additional compounds of this type having both acid-functional and ethylenically unsaturated components are described in U.S. Pat. No. 4,872,936 (Engelbrecht) and U.S. Pat. No. 5,130,347 (Mitra). A wide variety of such compounds containing both the ethylenically unsaturated and acid moieties can be used. Mixtures of such compounds can be used if desired.

Additional ethylenically unsaturated compounds with acid functionality include, for example, polymerizable bisphosphonic acids as disclosed for example, in U.S. Pat. Application Publication No. 2004/0206932 (Abuelyaman et al.); AA:ITA:IEM (copolymer of acrylic acid:itaconic acid with pendent methacrylate made by reacting AA:ITA copolymer with sufficient 2-isocyanatoethyl methacrylate to convert a portion of the acid groups of the copolymer to pendent methacrylate groups as described, for example, in Example 11 of U.S. Pat. No. 5,130,347 (Mitra)); and those recited in U.S. Pat. No. 4,259,075 (Yamauchi et al.), U.S. Pat. No. 4,499,251 (Omura et al.), U.S. Pat. No. 4,537,940 (Omura et al.), U.S. Pat. No. 4,539,382 (Omura et al.), U.S. Pat. No. 5,530,038 (Yamamoto et al.), U.S. Pat. No. 6,458,868 (Okada et al.), and European Pat. Application Publication Nos. EP 712,622 (Tokuyama Corp.) and EP 1,051,961 (Kuraray Co., Ltd.).

Compositions of the present invention can also include compositions that include combinations of ethylenically unsaturated compounds with acid functionality. Such compositions are self-adhesive and are non-aqueous. For example, such compositions can include: a first compound including at least one (meth)acryloxy group and at least one —O—P(O)(OH)$_x$ group, wherein x=1 or 2, and wherein the at least one —O—P(O)(OH)$_x$ group and the at least one (meth)acryloxy group are linked together by a C1-C4 hydrocarbon group; a second compound including at least one (meth)acryloxy group and at least one —O—P(O)(OH)$_x$ group, wherein x=1 or 2, and wherein the at least one —O—P(O)(OH)$_x$ group and the at least one (meth)acryloxy group are linked together by a C5-C12 hydrocarbon group; an ethylenically unsaturated compound without acid functionality; an initiator system; and a filler. Such compositions are described, for example, in PCT International Publication No. WO 2006/020760 A1 (Luchterhandt et al.).

The hardenable dental compositions can include at least 1 wt-%, at least 3 wt-%, or at least 5 wt-% ethylenically unsaturated compounds with acid functionality, based on the total weight of the unfilled composition. The compositions can include at most 80 wt-%, at most 70 wt-%, or at most 60 wt-% ethylenically unsaturated compounds with acid functionality.

The hardenable compositions of the present invention may include one or more hardenable components in the form of epoxy (oxirane) compounds (which contain cationically active epoxy groups) or vinyl ether compounds (which contain cationically active vinyl ether groups), thereby forming hardenable compositions.

Examples of epoxy (oxirane) compounds include organic compounds having an oxirane ring that is polymerizable by ring opening. These materials include monomeric epoxy compounds and epoxides of the polymeric type and can be aliphatic, cycloaliphatic, aromatic or heterocyclic. These compounds generally have, on the average, at least 1 polymerizable epoxy group per molecule, in some embodiments at least 1.5, and in other embodiments at least 2 polymerizable epoxy groups per molecule. The polymeric epoxides include linear polymers having terminal epoxy groups (e.g., a diglycidyl ether of a polyoxyalkylene glycol), polymers having skeletal oxirane units (e.g., polybutadiene polyepoxide), and polymers having pendent epoxy groups (e.g., a glycidyl methacrylate polymer or copolymer). The epoxides may be pure compounds or may be mixtures of compounds containing one, two, or more epoxy groups per molecule. The "average" number of epoxy groups per molecule is determined by dividing the total number of epoxy groups in the epoxy-containing material by the total number of epoxy-containing molecules present.

These epoxy-containing materials may vary from low molecular weight monomeric materials to high molecular weight polymers and may vary greatly in the nature of their backbone and substituent groups. Illustrative of permissible substituent groups include halogens, ester groups, ethers, sulfonate groups, siloxane groups, carbosilane groups, nitro groups, phosphate groups, and the like. The molecular weight of the epoxy-containing materials may vary from 58 to 100,000 or more.

Suitable epoxy-containing materials useful as the resin system reactive components in the present invention are listed in U.S. Pat. No. 6,187,836 (Oxman et al.) and U.S. Pat. No. 6,084,004 (Weinmann et al.).

Other suitable epoxy resins useful as the resin system reactive components include those which contain cyclohexene oxide groups such as epoxycyclohexanecarboxylates, typified by 3,4-epoxycyclohexylmethyl-3,4-epoxycyclohexanecarboxylate, 3,4-epoxy-2-methylcyclohexylmethyl-3,4-epoxy-2-methylcyclohexane carboxylate, and bis(3,4-epoxy-6-methylcyclohexyl-methyl) adipate. For a more detailed list of useful epoxides of this nature, reference is made to U.S. Pat. No. 5,037,861 (Crivello et al.), U.S. Pat. No. 6,245,828 (Weinmann et al.), and U.S. Pat. No. 6,779,656 (Klettke et al.).

Other epoxy resins that may be useful in the compositions of this invention include glycidyl ether monomers. Examples are glycidyl ethers of polyhydric phenols obtained by reacting a polyhydric phenol with an excess of chlorohydrin such as epichlorohydrin (e.g., the diglycidyl ether of 2,2-bis-(2,3-epoxypropoxyphenol)propane). Further examples of epoxides of this type are described in U.S. Pat. No. 3,018,262 (Schroeder), and in "Handbook of Epoxy Resins" by Lee and Neville, McGraw-Hill Book Co., New York (1967).

Other suitable epoxides useful as the resin system reactive components are those that contain silicon, useful examples of which are described in PCT International Publication No. WO 01/51540 (Klettke et al.).

Additional suitable epoxides useful as the resin system reactive components include octadecylene oxide, epichlorohydrin, styrene oxide, vinyl cyclohexene oxide, glycidol, glycidylmethacrylate, diglycidyl ether of Bisphenol A and other commercially available epoxides, as provided in U.S. Pat. No. 7,262,228 (Oxman et al.).

Blends of various epoxy-containing materials are also contemplated. Examples of such blends include two or more weight average molecular weight distributions of epoxy-containing compounds, such as low molecular weight (below 200), intermediate molecular weight (200 to 10,000) and higher molecular weight (above 10,000). Alternatively or additionally, the epoxy resin may contain a blend of epoxy-containing materials having different chemical natures, such as aliphatic and aromatic, or functionalities, such as polar and non-polar.

Other types of useful hardenable components having cationically active functional groups include vinyl ethers, oxetanes, spiro-orthocarbonates, spiro-orthoesters, and the like.

If desired, both cationically active and free radically active functional groups may be contained in a single molecule. Such molecules may be obtained, for example, by reacting a di- or poly-epoxide with one or more equivalents of an ethylenically unsaturated carboxylic acid. An example of such a material is the reaction product of Cyracure-6105 (available from Dow Chemical Co.) with one equivalent of methacrylic acid. Commercially available materials having epoxy and free-radically active functionalities include the CYCLOMER series, such as CYCLOMER M-100, M-101, or A-200 available from Daicel Chemical, Japan, and EBECRYL-3605 available from Radcure Specialties, UCB Chemicals, Atlanta, Ga.

The cationically curable components may further include a hydroxyl-containing organic material. Suitable hydroxyl-containing materials may be any organic material having hydroxyl functionality of at least 1 or 2. The hydroxyl-containing material contains two or more primary or secondary aliphatic hydroxyl groups (i.e., the hydroxyl group is bonded directly to a non-aromatic carbon atom). The hydroxyl groups can be terminally situated, or they can be pendent from a polymer or copolymer. The molecular weight of the hydroxyl-containing organic material can vary from very low (e.g., 32) to very high (e.g., one million or more). Suitable hydroxyl-containing materials can have low molecular weights (i.e., from 32 to 200), intermediate molecular weights (i.e., from 200 to 10,000), or high molecular weights (i.e., above 10,000). As used herein, all molecular weights are weight average molecular weights.

The hydroxyl-containing materials may be non-aromatic in nature or may contain aromatic functionality. The hydroxyl-containing material may optionally contain heteroatoms in the backbone of the molecule, such as nitrogen, oxygen, sulfur, and the like. The hydroxyl-containing material may, for example, be selected from naturally occurring or synthetically prepared cellulosic materials. The hydroxyl-containing material should be substantially free of groups which may be thermally or photolytically unstable; that is, the material should not decompose or liberate volatile components at temperatures below 100° C. or in the presence of actinic light which may be encountered during the desired photopolymerization conditions for the polymerizable compositions.

Suitable hydroxyl-containing materials useful in the present invention are listed in U.S. Pat. No. 6,187,836 (Oxman et al.).

The hardenable component(s) may also contain hydroxyl groups and cationically active functional groups in a single molecule. An example is a single molecule that includes both hydroxyl groups and epoxy groups.

The hardenable compositions of the present invention may include glass ionomer cements such as conventional glass ionomer cements that typically employ as their main ingredients a homopolymer or copolymer of an ethylenically unsaturated carboxylic acid (e.g., poly acrylic acid, copoly (acrylic, itaconic acid), and the like), a fluoroaluminosilicate ("FAS") glass, water, and a chelating agent such as tartaric acid. Conventional glass ionomers (i.e., glass ionomer cements) typically are supplied in powder/liquid formulations that are mixed just before use. The mixture will undergo self-hardening in the dark due to an ionic reaction between the acidic repeating units of the polycarboxylic acid and cations leached from the glass.

The glass ionomer cements may also include resin-modified glass ionomer ("RMGI") cements. Like a conventional glass ionomer, an RMGI cement employs an FAS glass. However, the organic portion of an RMGI is different. In one type of RMGI, the polycarboxylic acid is modified to replace or end-cap some of the acidic repeating units with pendent curable groups and a photoinitiator is added to provide a second cure mechanism, e.g., as described in U.S. Pat. No. 5,130,347 (Mitra). Acrylate or methacrylate groups are usually employed as the pendant curable group. In another type of RMGI, the cement includes a polycarboxylic acid, an acrylate or methacrylate-functional monomer and a photoinitiator, e.g., as in Mathis et al., "Properties of a New Glass Ionomer/Composite Resin Hybrid Restorative", Abstract No. 51, J. Dent Res., 66:113 (1987) and as in U.S. Pat. No. 5,063,257 (Akahane et al.), U.S. Pat. No. 5,520,725 (Kato et al.), U.S. Pat. No. 5,859,089 (Qian), U.S. Pat. No. 5,925,715 (Mitra) and U.S. Pat. No. 5,962,550 (Akahane et al.). In another type of RMGI, the cement may include a polycarboxylic acid, an acrylate or methacrylate-functional monomer, and a redox or other chemical cure system, e.g., as described in U.S. Pat. No. 5,154,762 (Mitra et al.), U.S. Pat. No. 5,520,725 (Kato et al.), and U.S. Pat. No. 5,871,360 (Kato). In another type of RMGI, the cement may include various monomer-containing or resin-containing components as described in U.S. Pat. No. 4,872,936 (Engelbrecht), U.S. Pat. No. 5,227,413 (Mitra), U.S. Pat. No. 5,367,002 (Huang et al.), and U.S. Pat. No. 5,965,632 (Orlowski). RMGI cements are typically formulated as powder/liquid or paste/paste systems, and contain water as mixed and applied. The compositions are able to harden in the dark due to the ionic reaction between the acidic repeating units of the polycarboxylic acid and cations leached from the glass, and commercial RMGI products typically also cure on exposure of the cement to light from a dental curing lamp. RMGI cements that contain a redox cure system and that can be cured in the dark without the use of actinic radiation are described in U.S. Pat. No. 6,765,038 (Mitra).

In certain embodiments, the compositions of the present invention are photopolymerizable, i.e., the compositions contain a photopolymerizable component and a photoinitiator (i.e., a photoinitiator system) that upon irradiation with actinic radiation initiates the polymerization (or hardening) of the composition. Such photopolymerizable compositions can be free radically polymerizable or cationically polymerizable.

Suitable photoinitiators (i.e., photoinitiator systems that include one or more compounds) for polymerizing free radically photopolymerizable compositions include binary and tertiary systems. Typical tertiary photoinitiators include an iodonium salt, a photosensitizer, and an electron donor compound as described in U.S. Pat. No. 5,545,676 (Palazzotto et al.). Preferred iodonium salts are the diaryl iodonium salts, e.g., diphenyliodonium chloride, diphenyliodonium hexafluorophosphate, diphenyliodonium tetrafluoroborate, and tolylcumyliodonium tetrakis(pentafluorophenyl)borate. Preferred photosensitizers are monoketones and diketones that absorb some light within a range of 400 nm to 520 nm (preferably, 450 nm to 500 nm). More preferred compounds are alpha diketones that have some light absorption within a range of 400 nm to 520 nm (even more preferably, 450 to 500 nm). Preferred compounds are camphorquinone, benzil, furil, 3,3,6,6-tetramethylcyclohexanedione, phenanthraquinone, 1-phenyl-1,2-propanedione and other 1-aryl-2-alkyl-1,2-ethanediones, and cyclic alpha diketones. Most preferred is camphorquinone. Preferred electron donor compounds include substituted amines, e.g., ethyl dimethylaminobenzoate. Other suitable tertiary photoinitiator systems useful for photopolymerizing cationically polymerizable resins are described, for example, in U.S. Pat. No. 6,765,036 (Dede et al.).

Other suitable photoinitiators for polymerizing free radically photopolymerizable compositions include the class of phosphine oxides that typically have a functional wavelength range of 380 nm to 1200 nm. Preferred phosphine oxide free radical initiators with a functional wavelength range of 380 nm to 450 nm are acyl and bisacyl phosphine oxides such as those described in U.S. Pat. No. 4,298,738 (Lechtken et al.), U.S. Pat. No. 4,324,744 (Lechtken et al.), U.S. Pat. No. 4,385,109 (Lechtken et al.), U.S. Pat. No. 4,710,523 (Lechtken et al.), and U.S. Pat. No. 4,737,593 (Ellrich et al.), U.S. Pat. No. 6,251,963 (Kohler et al.); and European Pat. Application Publication No. 0 173 567 A2 (Ying).

Commercially available phosphine oxide photoinitiators capable of free-radical initiation when irradiated at wavelength ranges of greater than 380 nm to 450 nm include bis(2,4,6-trimethylbenzoyl)phenyl phosphine oxide (IRGACURE 819, Ciba Specialty Chemicals, Tarrytown, N.Y.), bis (2,6-dimethoxybenzoyl)-(2,4,4-trimethylpentyl) phosphine oxide (CGI 403, Ciba Specialty Chemicals), a 25:75 mixture, by weight, of bis(2,6-dimethoxybenzoyl)-2,4,4-trimethylpentyl phosphine oxide and 2-hydroxy-2-methyl-1-phenyl-propan-1-one (IRGACURE 1700, Ciba Specialty Chemicals), a 1:1 mixture, by weight, of bis(2,4,6-trimethylbenzoyl)phenyl phosphine oxide and 2-hydroxy-2-methyl-1-phenylpropane-1-one (DAROCUR 4265, Ciba Specialty Chemicals), and ethyl 2,4,6-trimethylbenzylphenyl phosphinate (LUCIRIN LR8893X, BASF Corp., Charlotte, N.C.).

Typically, the phosphine oxide initiator is present in the photopolymerizable composition in catalytically effective amounts, such as from 0.1 weight percent to 5.0 weight percent, based on the total weight of the composition.

Tertiary amine reducing agents may be used in combination with an acylphosphine oxide. Illustrative tertiary amines useful in the invention include ethyl 4-(N,N-dimethylamino) benzoate and N,N-dimethylaminoethyl methacrylate. When present, the amine reducing agent is present in the photopolymerizable composition in an amount from 0.1 weight percent to 5.0 weight percent, based on the total weight of the composition. Useful amounts of other initiators are well known to those of skill in the art.

Suitable photoinitiators for polymerizing cationically photopolymerizable compositions include binary and tertiary systems. Typical tertiary photoinitiators include an iodonium salt, a photosensitizer, and an electron donor compound as described in EP 0 897 710 (Weinmann et al.); in U.S. Pat. No. 5,856,373 (Kaisaki et al.), U.S. Pat. No. 6,084,004 (Weinmann et al.), U.S. Pat. No. 6,187,833 (Oxman et al.), and U.S. Pat. No. 6,187,836 (Oxman et al.); and in U.S. Pat. No. 6,765,036 (Dede et al.). The compositions of the invention can include one or more anthracene-based compounds as electron donors. In some embodiments, the compositions comprise multiple substituted anthracene compounds or a combination of a substituted anthracene compound with unsubstituted anthracene. The combination of these mixed-anthracene electron donors as part of a photoinitiator system provides significantly enhanced cure depth and cure speed and temperature insensitivity when compared to comparable single-donor photoinitiator systems in the same matrix. Such compositions with anthracene-based electron donors are described in U.S. Pat. No. 7,262,228 (Oxman et al.).

Suitable iodonium salts include tolylcumyliodonium tetrakis(pentafluorophenyl)borate, tolylcumyliodonium tetrakis(3,5-bis(trifluoromethyl)-phenyl)borate, and the diaryl iodonium salts, e.g., diphenyliodonium chloride, diphenyliodonium hexafluorophosphate, diphenyliodonium hexafluoroantimonate, and diphenyliodonium tetrafluoroborate. Suitable photosensitizers include monoketones and diketones that absorb some light within a range of 450 nm to 520 nm (preferably, 450 nm to 500 nm). More suitable compounds include alpha diketones that have some light absorption within a range of 450 nm to 520 nm (even more preferably, 450 nm to 500 nm). Preferred compounds include camphorquinone, benzil, furil, 3,3,6,6-tetramethylcyclohexanedione, phenanthraquinone and other cyclic alpha diketones. Most preferred is camphorquinone. Suitable electron donor compounds include substituted amines, e.g., ethyl 4-(dimethylamino)benzoate and 2-butoxyethyl 4-(dimethylamino)benzoate; and polycondensed aromatic compounds (e.g. anthracene).

The initiator system is present in an amount sufficient to provide the desired rate of hardening (e.g., polymerizing and/or crosslinking). For a photoinitiator, this amount will be dependent in part on the light source, the thickness of the layer to be exposed to radiant energy, and the extinction coefficient of the photoinitiator. Preferably, the initiator system is present in a total amount of at least 0.01 wt-%, more preferably, at least 0.03 wt-%, and most preferably, at least 0.05 wt-%, based on the weight of the composition. Preferably, the initiator system is present in a total amount of no more than 10 wt-%, more preferably, no more than 5 wt-%, and most preferably, no more than 2.5 wt-%, based on the weight of the composition.

In certain embodiments, the compositions of the present invention are chemically hardenable, i.e., the compositions contain a chemically hardenable component and a chemical initiator (i.e., initiator system) that can polymerize, cure, or otherwise harden the composition without dependence on irradiation with actinic radiation. Such chemically hardenable compositions are sometimes referred to as "self-cure" compositions and may include glass ionomer cements, resin-modified glass ionomer cements, redox cure systems, and combinations thereof.

The chemically hardenable compositions may include redox cure systems that include a hardenable component (e.g., an ethylenically unsaturated polymerizable component) and redox agents that include an oxidizing agent and a reducing agent. Suitable hardenable components, redox agents, optional acid-functional components, and optional fillers that are useful in the present invention are described in U.S. Pat. No. 6,982,288 (Mitra et al.) and U.S. Pat. No. 7,173,074 (Mitra et al.).

The reducing and oxidizing agents should react with or otherwise cooperate with one another to produce free-radicals capable of initiating polymerization of the resin system (e.g., the ethylenically unsaturated component). This type of cure is a dark reaction, that is, it is not dependent on the presence of light and can proceed in the absence of light. The reducing and oxidizing agents are sufficiently shelf-stable and free of undesirable colorization to permit their storage and use under typical dental conditions. They should be sufficiently miscible with the resin system (and preferably water-soluble) to permit ready dissolution in (and discourage separation from) the other components of the hardenable composition.

Useful reducing agents include ascorbic acid, ascorbic acid derivatives, and metal complexed ascorbic acid compounds as described in U.S. Pat. No. 5,501,727 (Wang et al.); amines, especially tertiary amines, such as 4-tert-butyl dimethylaniline; aromatic sulfinic salts, such as p-toluenesulfinic salts and benzenesulfinic salts; thioureas, such as 1-ethyl-2-thiourea, tetraethyl thiourea, tetramethyl thiourea, 1,1-dibutyl thiourea, and 1,3-dibutyl thiourea; and mixtures thereof. Other secondary reducing agents may include cobalt (II) chloride, ferrous chloride, ferrous sulfate, hydrazine, hydroxylamine (depending on the choice of oxidizing agent), salts of a dithionite or sulfite anion, and mixtures thereof.

Suitable oxidizing agents will also be familiar to those skilled in the art, and include but are not limited to persulfuric acid and salts thereof, such as sodium, potassium, ammonium, cesium, and alkyl ammonium salts. Additional oxidizing agents include peroxides such as benzoyl peroxides, hydroperoxides such as cumyl hydroperoxide, t-butyl hydroperoxide, and amyl hydroperoxide, as well as salts of transition metals such as cobalt (III) chloride and ferric chloride, cerium (IV) sulfate, perboric acid and salts thereof, permanganic acid and salts thereof, perphosphoric acid and salts thereof, and mixtures thereof.

It may be desirable to use more than one oxidizing agent or more than one reducing agent. Small quantities of transition metal compounds may also be added to accelerate the rate of redox cure. In some embodiments a secondary ionic salt may be included to enhance the stability of the polymerizable composition as described in U.S. Pat. No. 6,982,288 (Mitra et al.).

The reducing and oxidizing agents are present in amounts sufficient to permit an adequate free-radical reaction rate. This can be evaluated by combining all of the ingredients of the hardenable composition except for the optional filler, and observing whether or not a hardened mass is obtained.

The reducing agent can be present in an amount of at least 0.01 wt-%, and typically at least 0.1 wt-%, based on the total weight (including water) of the components of the hardenable composition. The reducing agent is typically present in an amount of no greater than 10 wt-%, and more typically no greater than 5 wt-%, based on the total weight (including water) of the components of the hardenable composition.

The oxidizing agent is present in an amount of at least 0.01 wt-%, and typically at least 0.10 wt-%, based on the total weight (including water) of the components of the hardenable composition. The oxidizing agent is present in an amount of no greater than 10 wt-%, and typically no greater than 5 wt-%, based on the total weight (including water) of the components of the hardenable composition.

The reducing or oxidizing agents can be microencapsulated as described in U.S. Pat. No. 5,154,762 (Mitra et al.). This will generally enhance shelf stability of the hardenable composition, and if necessary permit packaging the reducing and oxidizing agents together. For example, through appropriate selection of an encapsulant, the oxidizing and reducing agents can be combined with an acid-functional component and optional filler and kept in a storage-stable state. Likewise, through appropriate selection of a water-insoluble encapsulant, the reducing and oxidizing agents can be combined with an FAS glass and water and maintained in a storage-stable state.

A redox cure system can be combined with other cure systems, e.g., with a hardenable composition such as described U.S. Pat. No. 5,154,762 (Mitra et al.).

In some embodiments, the dental compositions can have an initial color remarkably different than the cured dental structures. Color can be imparted to the composition through the use of a photobleachable or thermochromic dye. As used herein, "photobleachable" refers to loss of color upon exposure to actinic radiation. The composition can include at least 0.001 wt-% photobleachable or thermochromic dye, and typically at least 0.002 wt-% photobleachable or thermochromic dye, based on the total weight of the composition. The composition typically includes at most 1 wt-% photobleachable or thermochromic dye, and more typically at most 0.1 wt-% photobleachable or thermochromic dye, based on the total weight of the composition. The amount of photobleachable and/or thermochromic dye may vary depending on its extinction coefficient, the ability of the human eye to discern the initial color, and the desired color change. Suitable thermochromic dyes are disclosed, for example, in U.S. Pat. No. 6,670,436 (Burgath et al.).

For embodiments including a photobleachable dye, the color formation and bleaching characteristics of the photobleachable dye varies depending on a variety of factors including, for example, acid strength, dielectric constant, polarity, amount of oxygen, and moisture content in the atmosphere. However, the bleaching properties of the dye can be readily determined by irradiating the composition and evaluating the change in color. The photobleachable dye is generally at least partially soluble in a hardenable resin.

Exemplary classes of photobleachable dyes are disclosed, for example, in U.S. Pat. No. 6,331,080 (Cole et al.), U.S. Pat. No. 6,444,725 (Trom et al.), and U.S. Pat. No. 6,528,555 (Nikutowski et al.). Photobleachable dyes include, for example, Rose Bengal, Methylene Violet, Methylene Blue, Fluorescein, Eosin Yellow, Eosin Y, Ethyl Eosin, Eosin bluish, Eosin B, Erythrosin B, Erythrosin Yellowish Blend, Toluidine Blue, 4',5'-Dibromofluorescein, and combinations thereof.

The color change can be initiated by actinic radiation such as provided by a dental curing light which emits visible or near infrared (IR) light for a sufficient amount of time. The mechanism that initiates the color change in the compositions of the invention may be separate from or substantially simultaneous with the hardening mechanism that hardens the resin. For example, a composition may harden when polymerization is initiated chemically (e.g., redox initiation) or thermally, and the color change from an initial color to a final color may occur subsequent to the hardening process upon exposure to actinic radiation.

The change in composition color from exposure to actinic radiation from an initial color to a final color can be quantified by the same color test as used for evaluating staining resistance. Dental compositions can exhibit a color change, $\Delta E^*$, of at least 20; at least 30; or at least 40 from exposure to actinic radiation.

Optionally, compositions of the present invention may contain solvents (e.g., alcohols (e.g., propanol, ethanol), ketones (e.g., acetone, methyl ethyl ketone), esters (e.g., ethyl acetate), other nonaqueous solvents (e.g., dimethylformamide, dimethylacetamide, dimethylsulfoxide, 1-methyl-2-pyrrolidinone)), and water.

If desired, the compositions of the invention can contain additives such as indicators, dyes, pigments, inhibitors, accelerators, viscosity modifiers, wetting agents, buffering agents, stabilizers, and other similar ingredients that will be apparent to those skilled in the art. Viscosity modifiers include the thermally responsive viscosity modifiers (such as PLURONIC F-127 and F-108 available from BASF Wyandotte Corporation, Parsippany, N.J.) and may optionally include a polymerizable moiety on the modifier or a polymerizable component different than the modifier. Such thermally responsive viscosity modifiers are described in U.S. Pat. No. 6,669,927 (Trom et al.) and U.S. Pat. Application Publication No. 2004/0151691 (Oxman et al.).

Additionally, medicaments or other therapeutic substances can be optionally added to the dental compositions. Examples include, but are not limited to, fluoride sources, whitening agents, anticaries agents (e.g., xylitol), calcium sources, phosphorus sources, remineralizing agents (e.g., calcium phosphate compounds), enzymes, breath fresheners, anesthetics, clotting agents, acid neutralizers, chemotherapeutic agents, immune response modifiers, thixotropes, polyols, anti-inflammatory agents, antimicrobial agents (in addition to the antimicrobial lipid component), antifungal agents, agents for treating xerostomia, desensitizers, and the like, of the type often used in dental compositions. Combinations of any of the above additives may also be employed. The selection and amount of any one such additive can be selected by one of skill in the art to accomplish the desired result without undue experimentation.

The hardenable dental composition can be used to treat an oral surface such as tooth, as known in the art. The compositions can be hardened (e.g., polymerized) prior to applying the hardened dental composition or after applying the dental composition. For example, when the hardenable dental composition is used as a restorative such as a dental filling, the method generally comprises applying the hardenable composition to an oral surface (e.g. cavity); and hardening the hardenable composition. In yet other embodiments, a dental article such as a crown may be pre-formed from the hardenable dental composition described herein. The method of treating an oral surface may comprise providing the dental article and adhering the dental article to an oral (e.g. tooth) surface.

Another method of treating a tooth surface comprises providing a dental composition as described herein wherein the composition is in the form of a (partially hardened) hardenable, self-supporting, malleable structure having a first semi-finished shape; placing the hardenable dental composition on a tooth surface in the mouth of a subject; customizing the shape of the hardenable dental composition; and hardening the hardenable dental composition. The customization can occur in the patient's mouth or on a model outside the patient mouth such as described in US2003/0114553 (Karim et al.); incorporated herein by reference.

Objects and advantages of this invention are further illustrated by the following examples, but the particular materials and amounts thereof recited in these examples, as well as other conditions and details, should not be construed to unduly limit this invention. Unless otherwise indicated, all parts and percentages are on a weight basis.

Test Methods:

1. Post-Cure Flexural Strength (FS) Test

Flexural Strength was measured according to the following test procedure. A composition sample was pressed at 65° C. in a preheated mold to form a 2-mm×2-mm×25-mm test bar. The bar was aged at room temperature for 24 hours and light cured for 90 seconds by exposure to two oppositely disposed VISILUX Model 2500 blue light guns (3M Co.). The bar was then post-cured for 180 seconds in a Dentacolor XS unit (Kulzer, Inc., Germany) light box, and sanded lightly with 600-grit sandpaper to remove flash from the molding process. After storing in distilled water at 37° C. for 24 hours, the Flexural Strength and Flexural Modulus of the bar were measured on an Instron tester (Instron 4505, Instron Corp., Canton, Mass.) according to ANSI/ADA (American National Standard/American Dental Association) specification No. 27 (1993) at a crosshead speed of 0.75 mm/minute. Six bars of cured composite were prepared and measured with results reported in megapascals (MPa) as the average of the six measurements.

2. Pre-Cure Hardness Test

Samples (approximately 3 g each) of the dental compositions were pressed to a thickness of approximately 2 millimeters, using a hydraulic press (available from Carver Inc., Wabash, Ind.) at approximately 60° C. Each pressed sample was then stored at room temperature for 5 days, after which time the pre-cure hardness was measured at 28° C. and at 37° C. using a Model TA.Xt2i texture analyzer (manufactured by Texture Technologies Corp., Scarsdale, N.Y.). The texture analyzer was fitted with a cylindrical probe having a diameter of 2 millimeters. Each sample was allowed to thermally equilibrate at 28° C. for at least 20 minutes before each analysis was carried out. The flat end of the probe was pressed into each dental composition at a rate of 1 millimeter per second to a depth of 1 millimeter. A minimum of three samples of each composition were measured, with the average of the measurements reported.

3. Staining Test

Staining Disk Preparation

Samples (approximately 10 grams) of the dental compositions were pressed to a thickness of approximately 1.1 millimeters (between 2 pieces of silicone release paper), using a hydraulic press (available from Carver Inc., Wabash, Ind.) at approximately 60° C. Each pressed sample was then stored at room temperature for 5 days, after which a 14 mm diameter disc was cut and placed in a 1 mm thick by 15 mm diameter split mold, sandwiched between 2 pieces of 1 mil polyester film available from DuPont under the trade designation "Mylar". This was then placed between 2 steel plates, and pressed in the above hydraulic press at 37° C. for 2 minutes under 1000 psi (6.9×10⁶ Pa). The polyester film sandwiched sample was then taken out of the hydraulic press, covered with a 1 mm thick, 50 mm×75 mm glass microscope slide (VWR Catalog #374-1407) over the polyester film, and light cured for 50 seconds by using VISILUX Model 2500 dental curing light. After that, the other side was also cured for 50 seconds through a glass microscope slide. With the polyester films still present, the dental composite disc was conditioned in a 37° C. oven for 15 minutes. This sample disc was then stored in 37° C. deionized water before staining test.

Coffee Solution

A 15% coffee solution was prepared by adding 15 g of Folgers Classic Roast Instant Coffee Crystals to 85 g of 80° C. de-ionized water, mixing well, and then letting it cool down to 37° C. or less. (coffee crystals commercially available from The Folger Coffee Company, Cincinnati, Ohio 45202).

Mustard/Ketchup Solution

A 12.5% mustard (Roundy's Supermarket, Inc., Milwaukee, Wis.) and 12.5% ketchup (H.J. Heinz Co. L.P., Pittsburgh, Pa.) solution was prepared with deionized water.

Red Wine

The following red wine was used: Turning Leaf MERLOT 2006 reserve, from Turning Leaf Vineyard, Modesto, Calif.

Two discs were used from each formulation for the staining test. The CIELAB color of each disc was measured before the staining test as follows. A spectrophotometer obtained from HunterLab, Reston, Va. under the trade designation "UltraScan XE" in small area view mode with RSIN (reflectance specular included) was used to measure the L*, a*, and b* values. After the initial color measurements, the dental composite discs were placed in the indicated test solution for the specified duration of time. The stained discs were then rinsed with de-ionized water, and the color of the stained discs was measured again. The staining resistance is reported as ΔE* as defined below:

$$\Delta E^* = [(L_0^* - L_1^*)^2 + (a_0^* - a_1^*)^2 + (b_0^* - b_1^*)^2]^{1/2}$$

wherein each 0 represents the initial values and each 1 represents the values after conditioning the hardened dental composition in the indicated test solution.

4. Refractive Index Measurement

Refractive Index was measured at Room Temperature on a Refractometer manufactured by Bausch & Lomb (Rochester, N.Y., USA), Cat. No. 33.46.10

Components Employed in the Examples

1. Preparation of 2-[2'-(2-hydroxyethoxy)biphenyl-2-yloxy]ethanol

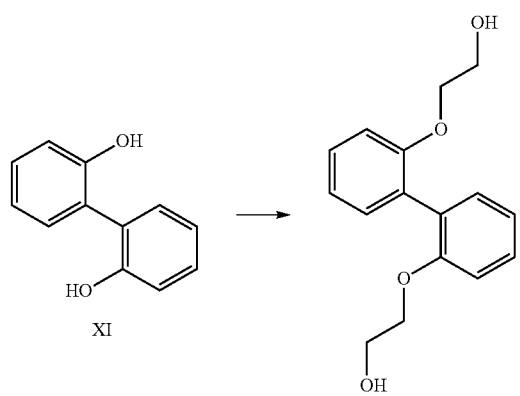

XI

To a 12000 ml 3 neck round bottom equipped with an overhead stirrer, heating mantle, temperature probe, and condenser with gas bubbler was added 2421 g. biphenyl-2,2'-diol (XI), 2519 g. ethylene carbonate, 24.2 g. potassium iodide, and 50 g. N,N-dimethlformamide (DMF). The reaction was stirred well and heated to 140° C. The reaction was monitored by the amount of gas released and gas chromatography (GC). After 4 hours the reaction was ~70% starting material. The temperature was increased to 150° C. After an additional 4 hours the starting material and mono substituted intermediate were reacted. The reaction was cooled to 40° C. and 2000 ml ethyl acetate was added. The reaction mixture was washed 3 times with 500 ml water/sodium chloride (brine). The organic layer was dried over MgSO₄, filtered and concentrated under vacuum to recover a dark brown oil. The yield was 3400 g.

The material was distilled on a roll film short path distillation apparatus, with the following conditions: Feed 80° C.; Jacket 160° C.; Condenser 75° C.; –300 RPM roll speed; 20 microns vacuum. The first pass recovered 2700 g yellow-orange clear oil which solidified upon cooling. GC analysis showed this was 97% of the desired product, 2-[2'-(2-hydroxyethoxy)biphenyl-2-yloxy]ethanol (XII).

2. Preparation of 2-[2-(2'-{2-[2-(methacryloyloxy)ethylcarbamoyloxy]ethoxy}biphenyl-2-yloxy)ethoxycarbonylamino]ethyl methacrylate ("DEBP-IEM")

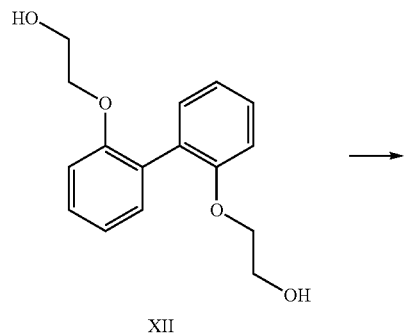

XII

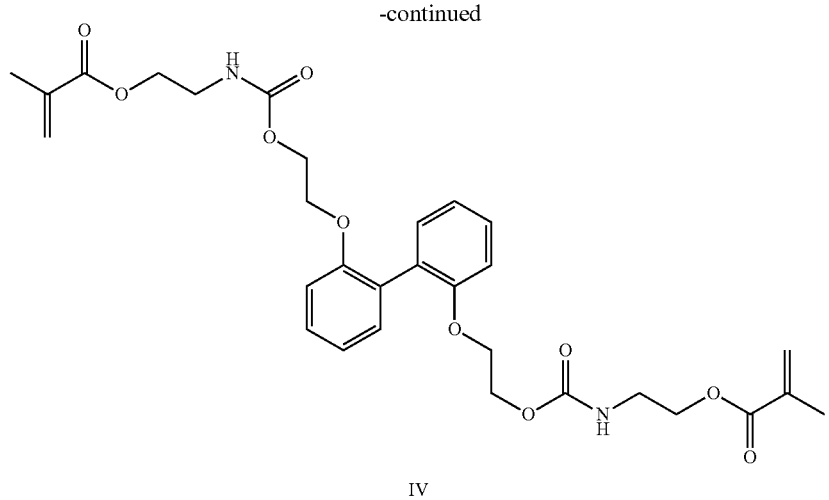

IV

To a 2000 ml 3 neck round bottom equipped with mechanical agitation, temperature probe, and condenser was added 120 g 2-[2'-(2-hydroxyethoxy)biphenyl-2-yloxy]ethanol (XII), 984 g cyclohexane, 256 g isopropyl acetate, 0.12 g 2,6-di-tert-butyl-4-methylphenol (BHT), 135.7 g isocyanatoethyl methacrylate (IEM), and 0.138 g of dibutyl tin dilaurate (DBTDL). The reaction mixture was heated to 75° C. and maintained at that temperature for 16 hours at which time analysis by thin layer chromatography (TLC) indicated that the reaction was not complete. An additional charge of DBTDL was added and the reaction mixture was maintained at 75° C. for 12 hours at which time analysis by TLC indicated that the reaction was not complete. An additional charge of DBTDL was added and the reaction mixture was maintained at 75° C. for 8 hours at which time analysis by TLC indicated that the reaction was complete. The reaction mixture was allowed to cool to ambient temperature and was stirred overnight. A white solid was isolated by filtration, washed with heptanes, and then air dried to provide 230 g of the desired product 2-[2-(2'-{2-[2-(methacryloyloxy)ethylcarbamoyloxy]ethoxy}biphenyl-2-yloxy)ethoxycarbonylamino]ethyl methacrylate as a white crystalline solid, m.p. 72-74° C. Analysis by nuclear magnetic resonance spectroscopy indicated >95% purity.

3. Preparation of 6-[2'-(6-hydroxy-hexyloxy)-biphenyl-2-yloxy]-hexan-1-ol ("6,6'-DHBP diol")

To a 3000 ml 3 neck round bottom equipped with an overhead stirrer, heating mantle, temperature probe, and condenser was added 150 g. biphenyl-2,2'-diol, 1016 g. DI H$_2$O, 24.15 g. NaI, and 258 g. 50% NaOH in H$_2$O. The reaction was stirred well and heated to 100° C. Over a 90 minute period, to the reaction was added dropwise through an addition funnel 440.2 g. 6-chlorohexanol. Continued to heat for a total of 4 hours, at which time TLC showed no starting material, and a small amount of monoalkylated intermediate. Added 25 g. additional 50% NaOH in H$_2$O and heated for 4 more hours. TLC showed the reaction was complete. Cooled to room temperature.

To the batch 1000 grams ethyl acetate was added and stirred well. Phase split and removed the lower aqueous layer. Added 500 g. H$_2$O and 20 g. con HCl and shake and phase split and removed the lower aqueous layer. The reaction mixture was washed 2 times with 500 ml water/sodium chloride (brine). The ethyl acetate was dried over MgSO$_4$, filtered and concentrated in-vacuo to recover a yellow oil. The yield was 480 g.

The material was placed in a one-liter three-neck flask with a temperature probe and magnetic stirrer and distillation head without column. Pulled vacuum to remove residual 6-chlorohexanol. Heated to 200° C. and 2 mm Hg for a total of one hour after no more distillate came over to complete the purification.

4. Preparation of 2-[6-(2'-{6-[2-(methacryloyloxy)ethylcarbamoyloxy]hexyloxy}biphenyl-2-yloxy)hexyloxycarbonylamino]ethyl methacrylate ("DHBP-DIEM")

To a 2000 ml 3 neck round bottom equipped with an overhead stirrer, heating mantle, temperature probe, and condenser was added 100 grams 6,6'-DHBP diol, 475 g. toluene, 0.07 g. BHT, 0.08 g. dibutyltin dilaurate and 80.3 g. isocyanatoethyl methacrylate (IEM). Heat the reaction to 75° C. and hold for four hours. Added 4 g. IEM and 5 drops additional DBTDL and held at 75° C. for four hours. TLC and GC indicated the reaction was complete. Stripped the solvent on a rotary evaporator using an air sparge to give 190 g. of the amber colored crude product oil.

Passed 75 g. of the crude product through a short flash silica gel column using ethyl acetate/hexane mixtures to elute the pure product fractions. To these added 250 ppm BHT inhibitor. The solvent was removed using a rotary evaporator with an air sparge placed into the product, and finished by heating to 50° C. while pulling 1 mm Hg vacuum on the system. The yield was 59 g. of a light yellow-green oil that was determined to be the desired product, 2-[6-(2'-{6-[2-(methacryloyloxy)ethylcarbamoyloxy]hexyloxy}biphenyl-2-yloxy)hexyloxycarbonylamino]ethyl methacrylate, by NMR characterization. The refractive index of the DHBP-IEM was determined to be 1.5180.

| Abbreviation | Chemical Description (Supplier, Location) |
|---|---|
| | Polymerizable Monomer |
| UDMA | Diurethane Dimethacrylate CAS # 72869-86-4 2-Propenoic acid, 2-methyl-, 7,7,9(or 7,9,9)trimethyl- |

-continued

| Abbreviation | Chemical Description (Supplier, Location) |
|---|---|
| | 4,13-dioxo 3,14-dioxa-5, 12-diazahexadecane-1,16-diyl ester, available from Dajac Laboratories |
| Procrylate | 2,2,-bis-4-(3-hydroxy-propoxy-phenyl)propane dimethacrylate (also described as "Procrylat") |
| TEGDMA | triethyleneglycol dimethacrylate |
| | Inorganic Filler |
| Nano-Cluster | Refers to silane-treated zirconia/silica nanocluster filler prepared essentially as described in U.S. Pat. No. 6,730,156 (Preparatory Example A (line 51-64) and Example B (column 25 line 65 through column 26 line 40). |
| 20 nm Nanomer | Refers to silane-treated nano-sized silica having a nominal particle size of approximately 20 nanometers, prepared essentially as described in U.S. Pat. No. 6,572,693 B1, (column 21, lines 63-67 for Nanosized particle filler, Type #2. |
| M5 | hydrophilic fumed (pyrogenic) silica (Cab-O-Sil M5, Cabot Corp. Tuscola, IL) |
| | Components of Photointiator Package |
| TINUVIN | Benzotriazole polymerizable UV stabilizer available under the trade designation "TINUVIN R 796" (Ciba Specialty Chemicals, Tarrytown, NY) |
| BHT | 2,6-di-tert-butyl-4-methylphenol (Sigma-Aldrich Fine Chemicals, St. Louis, MO) |
| CPQ | camphorquinone (Sigma-Aldrich) |
| DPIHFP | "DPIHFP" refers to diphenyl iodonium hexafluorophosphate; |
| EDMAB | ethyl 4-(N,N-dimethylamino)benzoate (Sigma-Aldrich) |
| | Pigments |
| Red Pigment | a dispersion containing a red iron III oxide pigment |
| Yellow Pigment | a dispersion containing a yellow iron III oxide pigment |
| White Pigment | a dispersion containing a rutile titanium dioxide pigment |

Part 1
Polymerizable Monomer Photoinitiator Activation Package A and Dental Compositions Made from this Photoinitiator Package A

TABLE 1

| Photoinitiator Activation Package A | |
|---|---|
| Activators | Weight (gram) |
| TINUVIN | 0.2327 |
| BHT | 0.02328 |
| EDMAB | 0.1551 |
| DPIHFP | 0.07758 |
| CPQ | 0.02637 |
| Polymerizable monomers DEBP-IEM or DEHP-IEM or UDMA or Procrylate | 15.00 g |

Note:
Polymerizable monomers used in Examples E1, E2 and E3 were all activated with photoinitiator package A shown above in Table 1.

2. DEBP-IEM and DEHP-IEM Resin Activation (with Photoinitiator Package A)

The photoinitiator components and DEBP-IEM (Table 1) or DEHP-IEM were placed in a MAX 20 plastic mixing cup having a screw cap (Flakteck, Landrum, S.C.) and the closed cup was heated in an oven at 85° C. for 10 minutes (until melting of all DEBP-IEM was complete). The cup was placed in a DAC 150 FV speed mixer (Flakteck) and spin mixing was carried out for 3 min at 3000 rpm to dissolve all photoinitiator components.

3. UDMA Resin Activation (with Photoinitiator Package A)

The photoinitiator components and UDMA (Table 1) were placed in a MAX 20 plastic mixing cup having a screw cap (Flakteck, Landrum, S.C.) and the closed cup was heated in an oven at 85° C. for 10 minutes. The cup was placed in a DAC 150 FV speed mixer (Flakteck) and spin mixing was carried out for 3 min at 3000 rpm to dissolve all photoinitiator components.

4. Procrylate Resin Activation (with Photoinitiator Package A)

The photoinitiator components and Procrylate were combined in the same manner as the UDMA Resin Activation, substituting the UDMA with Procrylate.

Dental Composition Paste Preparation Procedure

The activated resins (as described above, see Table 2 for quantities) were placed in a MAX 100 plastic mixing cup having a screw cap (Flakteck, Landrum, S.C.). This closed MAX cup was heated in an 85° C. oven for 5 minutes, and was then placed in a DAC 150 FV speed mixer (Flakteck) and spin mixing was carried out for 1 minute at 3000 rpm to mix the resins. After that, the fillers were added to the MAX cup; the closed MAX cup was heated in an 85° C. oven for 10 minutes, and was then placed in a DAC 150 FV speed mixer (Flakteck) and spin mixing was carried out for 1 minute at 3000 rpm; this spin mix was repeated twice (1 minute at 3000 rpm). The resulting pastes were testing according to the previously described test methods; data are shown in Table 3.

TABLE 2

Dental Composite Examples E1, E2 and E3

| Ex | DEBP-IEM | Procrylate | UDMA | Nano-Cluster | 20 nm Nanomer | M5 |
|---|---|---|---|---|---|---|
| E1 | 4.5544 g | 4.5544 g | 4.5544 g | 40.2408 g | 4.4712 g | 1.6250 g |
| E2 | 4.4135 g | 4.4135 g | 4.4135 g | 41.2385 g | 4.5821 g | 0.9391 g |
| E3 | 4.2868 g | 4.2868 g | 4.2868 g | 42.2133 g | 4.6904 g | 0.2361 g |

Dental Composite Examples E4

| Ex | DHBP-IEM | Nano-Cluster | 20 nm Nanomer |
|---|---|---|---|
| E4 | 3.6000 g | 10.2600 g | 1.1400g |

TABLE 3

Physical Properties-E1, E2, E3, and E4

| | E1 | E2 | E3 | Commercially Available Control 1 | E4 |
|---|---|---|---|---|---|
| Pre-cure Hardness | 1681 ± 40 | 1623 ± 50 | 1559 ± 36 | 1450 | 264 +/− 7 |
| Flexural Strength (MPa) | 134 ± 7 | 144 ± 19 | 136 ± 12 | 132 | 122 +/− 16 |
| Flexural Modulus (MPa) | 8815 ± 272 | 10605 ± 2415 | 8894 ± 212 | 7316 | |

The results show that the compositions comprising DEBP-IEM and DHEP-IEM exhibited suitable properties for use in hardenable dental compositions and articles.

Crown Formation and Handling Assessment

Crowns were prepared by a two-stage process, analogous to that described in patent application US2005100868. Samples of each paste to be tested were injected into a cavity lined with an ethylene-vinyl acetate (EVA) copolymer film, containing ~19% vinyl acetate. This sample of paste was transferred to a second multi-part mold, covered with a second polyethylene film, and compression molded to form a hollow crown shape. This mold was in the form of a symmetric model lower first molar. The resulting formed crown had a mesial-distal dimension of approximately 10.6 mm.

The materials were evaluated by an experienced dentist customizing the crowns formed of the materials on a prepared artificial tooth in a Columbia Dentoform R862 Typodont, at the #31 position. The Typodont tooth was modified to have a shoulder preparation. The crown was wet with water, manipulated by hand to obtain an initial assessment of the handling, and adapted to the preparation in the Typodont. Each of the formulations E1-E3 were evaluated and demonstrated acceptable handling, based on the ability to trim, adjust, and smooth the crown before cure, in comparison to a commercially available material.

Part 2

Polymerizable Monomer Photoinitiator Activation Package B and Dental Compositions Made from this Photoinitiator Package B Resins containing a slightly modified photoinitiator package B were prepared (Table 4). The resin activation procedure is the same as shown in Part 1.

TABLE 4

Photoinitiator Activation Package B

| Activators | Weight (gram) |
|---|---|
| TINUVIN | 0.2337 |
| BHT | 0.02337 |
| EDMAB | 0.1558 |
| DPIHFP | 0.1246 |
| CPQ | 0.04238 |
| Polymerizable monomers DEBP-IEM or UDMA or Procrylate or TEGDMA | 15.00 g |

Dental Composition Paste Preparation Procedure

Red pigment (0.0015 g), yellow pigment (0.0064 g) and white pigment (0.0200 g) were placed in a MAX 20 plastic mixing cup having a screw cap (Flakteck, Landrum, S.C.), followed by adding the indicated activated resins (as described above in Table 4). The closed MAX cup was heated in an 85° C. oven for 5 minutes, and was then placed in a DAC 150 FV speed mixer (Flakteck) and spin mixing was carried out for 1 minute at 3000 rpm to mix pigments and resins. After that, the fillers were added to the MAX cup; the closed MAX cup was heated in an 85° C. oven for 10 minutes, and was then placed in a DAC 150 FV speed mixer (Flakteck) and spin mixing was carried out for 1 minute at 3000 rpm; the spin mix cycle was repeated twice (1 minute at 3000 rpm). The resulting pastes were testing according to the previously described test methods.

TABLE 5

Dental Composite Examples E4 and E5

| Ex | DEBP-IEM | Procrylate | UDMA | TEGDMA | Nano-cluster | 20 nm Nanomer | M5 |
|---|---|---|---|---|---|---|---|
| E4 | 1.2000 g | 1.2000 g | 1.2000 g | 0.0000 g | 10.1574 g | 1.1286 g | 0.1140 g |
| E5 | 1.0800 g | 1.8000 g | 0.0000 g | 0.7200 g | 10.1574 g | 1.1286 g | 0.1140 g |

The hardened dental compositions of E4 and E5 were also evaluated for staining resistance. The results are reported in Tables 6-8 as follow:

TABLE 6

Staining in Coffee Solution

| | E4 Delta E* | E5 Delta E* | Commercially Available Control 2 |
|---|---|---|---|
| 3 Days | 3.24 ± 0.29 | 3.74 ± 0.52 | 10.39 ± 0.47 |

TABLE 7

Staining in Mustard/Ketchup Solution

| | E4 Delta E* | E5 Delta E* | Commercially Available Control 2 |
|---|---|---|---|
| 1 hour | 3.08 ± 0.89 | 2.79 ± 1.71 | 8.09 ± 0.21 |
| 2 hours | 5.29 ± 1.20 | 3.75 ± 1.13 | 13.71 ± 0.55 |
| 4 hours | 7.31 ± 1.28 | 6.64 ± 1.98 | 19.89 ± 1.13 |

TABLE 8

Staining in Red Wine

| | E4 Delta E* | E5 Delta E* | Commercially Available Control 2 |
|---|---|---|---|
| 1 Day | 0.81 ± 0.09 | 0.30 ± 0.15 | 5.46 ± 0.56 |
| 3 Days | 1.49 ± 0.12 | 0.47 ± 0.08 | 8.45 ± 1.07 |
| 7 Days | 2.33 ± 0.05 | 0.63 ± 0.13 | 10.97 ± 0.93 |

What is claimed is:

1. A hardenable dental composition comprising at least one biphenyl monomer having the general structure

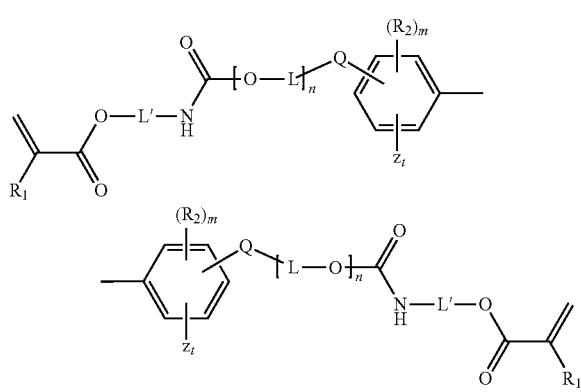

wherein $R_2$ is independently a halogen or a $C_1$ to $C_4$ alkyl group;

m ranges from 0 to 4;

z is an aromatic ring;

t is independently 0;

Q is independently O or S;

L is independently a $C_2$ to $C_{12}$ alkylene group optionally substituted with one or more hydroxyl groups;

n independently ranges from 0 to 10;

L' is independently a $C_2$ to $C_{12}$ alkylene group; and $R_1$ is independently H or methyl.

2. The hardenable dental composition of claim 1 wherein each substituent has a molecular weight of less than 500 g/mole.

3. The hardenable dental composition of claim 1 wherein the substituents further comprise an alkoxy group.

4. The hardenable dental composition of claim 1 wherein the substituents are bonded at an ortho position of the aromatic rings.

5. The hardenable dental composition of claim 1 wherein the biphenyl monomer is a solid at 25° C.

6. The hardenable dental composition of claim 5 wherein the dental composition further comprises at least one other ethylenically unsaturated monomer that is a liquid at 25° C.

7. The hardenable dental composition of claim 1 wherein the biphenyl monomer is a liquid at 25° C.

8. The hardenable dental composition of claim 1 wherein the composition further comprises at least one filler.

9. The hardenable dental composition of claim 8 wherein the filler comprises inorganic nanoparticles.

10. The hardenable dental composition of claim 9 wherein the inorganic nanoparticles comprise silica, zirconia, or mixtures thereof.

11. The hardenable dental composition of claim 9 wherein the nanoparticles are in the form of nanoclusters.

12. The hardenable dental composition of claim 1 wherein Q is oxygen.

13. The hardenable dental composition of claim 1 wherein m is 0.

14. The hardenable dental composition of claim 1 wherein n is 1 and L ranges from C2 to C8.

15. A dental article comprising the hardenable dental composition of claim 1 at least partially hardened.

16. A dental article comprising the hardenable dental composition of claim 1 wherein the composition is in the form self-supporting, malleable structure having a first semi-finished shape.

17. A method of treating a tooth surface, the method comprising providing a hardenable dental composition according to claim 1, wherein the composition is in the form self-supporting, malleable structure having a first semi-finished shape;

placing the hardenable dental composition on a tooth surface in the mouth of a subject;

customizing the shape of the hardenable dental composition; and hardening or partially hardening the hardenable dental composition.

18. A biphenyl di(meth)acrylate monomer having the general structure

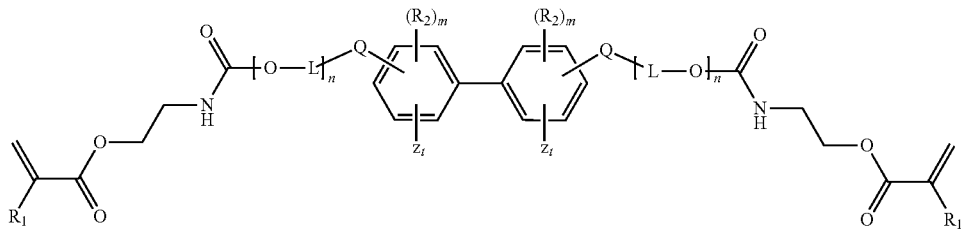

wherein $R_2$ is independently Br or a $C_1$ to $C_4$ alkyl group; m ranges from 0 to 4;

z is an aromatic ring;

t is independently 0;

Q is independently O or S;

L is independently a $C_2$ to $C_{12}$ alkylene group optionally substituted with one or more hydroxyl groups;

n independently ranges from 0 to 10; and wherein $R_1$ is independently H or methyl.

19. The biphenyl di(meth)acrylate monomer of claim 1 wherein the biphenyl di(meth)acrylate monomer is a liquid at 25° C.

* * * * *